(12) United States Patent
Osawa

(10) Patent No.: US 11,546,541 B2
(45) Date of Patent: Jan. 3, 2023

(54) SEMICONDUCTOR DEVICE

(71) Applicant: OLYMPUS CORPORATION, Hachioji (JP)

(72) Inventor: Masato Osawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 70 days.

(21) Appl. No.: 17/189,748

(22) Filed: Mar. 2, 2021

(65) Prior Publication Data
US 2021/0185262 A1 Jun. 17, 2021

Related U.S. Application Data

(63) Continuation of application No. PCT/JP2018/033379, filed on Sep. 10, 2018.

(51) Int. Cl.
*H04N 5/3745* (2011.01)
*A61B 1/05* (2006.01)
(Continued)

(52) U.S. Cl.
CPC ........... *H04N 5/37457* (2013.01); *A61B 1/05* (2013.01); *H04N 5/225* (2013.01); *H04N 5/363* (2013.01);
(Continued)

(58) Field of Classification Search
None
See application file for complete search history.

(56) References Cited

U.S. PATENT DOCUMENTS

2016/0301886 A1 10/2016 Muto et al.
2017/0318250 A1 11/2017 Sakakibara et al.
(Continued)

FOREIGN PATENT DOCUMENTS

JP 2005-311487 A 11/2005
JP 2007-306348 A 11/2007
(Continued)

OTHER PUBLICATIONS

EPO, Machine Translation of JP2007-306348 A (Year: 2022).*
(Continued)

*Primary Examiner* — David N Werner
(74) *Attorney, Agent, or Firm* — WHDA, LLP

(57) ABSTRACT

A semiconductor device according to an embodiment includes a plurality of element arrays, a signal-processing circuit, and a comparison-voltage generation circuit. Each element array is selectively connected to a vertical signal line and includes an amplification transistor configured to output a first analog signal on the basis of an input analog voltage and an actual value of variation of a characteristic value of each element array included in the plurality of element arrays. The comparison-voltage generation circuit is configured to output a gradually increasing or gradually decreasing comparison voltage. The signal-processing circuit includes a storage circuit and is configured to compare the first analog signal with the comparison voltage and store a timing at which the comparison voltage and a value of a second analog signal generated by adding a predetermined absolute value to the first analog signal match each other onto the storage circuit.

15 Claims, 11 Drawing Sheets

(51) Int. Cl.
- *H04N 5/225* (2006.01)
- *H04N 5/376* (2011.01)
- *H04N 5/378* (2011.01)
- *H04N 5/374* (2011.01)
- *H04N 5/363* (2011.01)
- *H04N 5/369* (2011.01)

(52) U.S. Cl.
CPC ........... *H04N 5/369* (2013.01); *H04N 5/3692* (2013.01); *H04N 5/3698* (2013.01); *H04N 5/374* (2013.01); *H04N 5/378* (2013.01); *H04N 5/3745* (2013.01); *H04N 5/3765* (2013.01); *H04N 5/37455* (2013.01); *H04N 2005/2255* (2013.01)

(56) References Cited

U.S. PATENT DOCUMENTS

| | | | | |
|---|---|---|---|---|
| 2018/0122852 A1* | 5/2018 | Nishimura | ......... | H01L 27/14623 |
| 2020/0036930 A1* | 1/2020 | Hanzawa | ............... | H04N 5/376 |
| 2021/0185262 A1* | 6/2021 | Osawa | .................. | H04N 5/225 |
| 2022/0141411 A1* | 5/2022 | Sato | .................. | H01L 27/14612 348/308 |
| 2022/0174231 A1* | 6/2022 | Akebono | ................. | H03K 5/08 |
| 2022/0303491 A1* | 9/2022 | Yamazaki | ................. | G06T 7/50 |

FOREIGN PATENT DOCUMENTS

| | | |
|---|---|---|
| JP | 2014-197772 A | 10/2014 |
| JP | 2016-12903 A | 1/2016 |
| JP | 2016-92661 A | 5/2016 |
| JP | 2016-201649 A | 12/2016 |
| JP | 2018-007035 A | 1/2018 |
| JP | 2018-078281 A | 5/2018 |
| WO | 2011/030391 A1 | 3/2011 |

OTHER PUBLICATIONS

WIPO, Int'l Preliminary Report on Patentability for PCT/JP2018/033379 (Year: 2018).*

JPO, Notice of Reasons for Refusal for Japanese Patent Application No. 2020-546547 (Year: 2022).*

International Search Report dated Nov. 27, 2018, issued in counterpart International Application No. PCT/JP2018/033379, w/English translation (2 pages).

* cited by examiner

SEMICONDUCTOR DEVICE

The present application is a continuation application based on International Patent Application No. PCT/JP2018/033379 filed on Sep. 10, 2018, the content of which is incorporated herein by reference.

BACKGROUND OF THE INVENTION

Field of the Invention

The present invention relates to a semiconductor device.

Description of Related Art

As a semiconductor device (solid-state imaging device). CMOS image sensors that are produced by using a similar process to that used for CMOS integrated circuits have been developed. One such CMOS image sensor is an image sensor using a column analog-to-digital converter (ADC) that converts an analog signal output from a pixel into a digital signal while suppressing fixed-pattern noise of the pixel by using analog-to-digital (AD) conversion circuits that perform processing in parallel for each pixel column of the pixel array, as disclosed in Japanese Unexamined Patent Application, First Publication No. 2005-311487.

SUMMARY OF THE INVENTION

According to a first aspect of the present invention, a semiconductor device includes a plurality of element arrays, a signal-processing circuit, and a comparison-voltage generation circuit. Each element array included in the plurality of element arrays is selectively connected to a vertical signal line and includes an amplification transistor configured to output a first analog signal on the basis of an input analog voltage and an actual value of variation of a characteristic value of each element array included in the plurality of element arrays. The signal-processing circuit is connected to the vertical signal line. The comparison-voltage generation circuit is configured to output a gradually increasing or gradually decreasing comparison voltage to the signal-processing circuit. The signal-processing circuit includes a storage circuit and is configured to compare the first analog signal with the comparison voltage and store a timing at which the comparison voltage and a value of a second analog signal generated by adding a predetermined absolute value to the first analog signal match each other onto the storage circuit. The signal-processing circuit includes a differential transistor forming a differential pair with the amplification transistor of the element array included in the plurality of element arrays when the element array and the signal-processing circuit are connected to each other by the vertical signal line. The signal-processing circuit is configured to output a difference between the comparison voltage input to the differential transistor and the analog voltage input to the amplification transistor.

According to a second aspect of the present invention, in the first aspect, a threshold voltage of the differential transistor may be smaller than a threshold voltage of the amplification transistor.

According to a third aspect of the present invention, in the first aspect, an aspect ratio of W (channel width)/L (channel length) of the differential transistor may be greater than an aspect ratio of W/L of the amplification transistor.

According to a fourth aspect of the present invention, in the first aspect, the semiconductor device may further include a level-shift circuit that is provided between the amplification transistor and a tail current source of the signal-processing circuit and is configured to cause a source voltage of the amplification transistor to be higher than a source voltage of the differential transistor.

According to a fifth aspect of the present invention, in the first aspect, a back gate terminal of the differential transistor may be biased to the same voltage as that of a source terminal of the differential transistor. A back gate terminal of the amplification transistor may be biased to a lower voltage than a voltage of a source terminal of the differential transistor.

According to a sixth aspect of the present invention, in the first aspect, a bias current of an active load provided in the signal-processing circuit may be smaller than half of a tail current output by a tail current source of the signal-processing circuit.

According to a seventh aspect of the present invention, in the sixth aspect, the signal-processing circuit may be configured to compare the first analog signal with the comparison voltage in a first period in which the bias current of the active load is less than half of the tail current. The signal-processing circuit may be configured to perform a reset operation in a second period in which the bias current of the active load is greater than half of the tail current.

According to an eighth aspect of the present invention, in the first aspect, the predetermined absolute value may be greater than or equal to 30 mV and less than or equal to 500 mV.

According to a ninth aspect of the present invention, in the first aspect, the semiconductor device may be applied to an endoscope including an insertion unit capable of being inserted into a subject and a connector unit detachably connected to a control device that executes predetermined image processing and is provided in a distal end part of the insertion unit. The semiconductor device may further include a first memory, a second memory, a subtractor, and a low-voltage differential-signaling (LVDS) driver. The first memory is configured to store digital data corresponding to the analog voltage at a timing at which the value of the second analog signal and the comparison voltage match each other when the analog voltage is at reset voltage. The second memory is configured to store digital data corresponding to the analog voltage at a timing at which the value of the second analog signal and the comparison voltage match each other when the analog voltage is at video voltage. The subtractor is configured to subtract digital data corresponding to an element in the plurality of element arrays among digital data stored on the first memory front the digital data corresponding to the element stored on the second memory so as to generate image data. The LVDS driver is configured to convert the image data into a differential signal and transmit the differential signal to the connector unit through two transmission lines.

DETAILED DESCRIPTION OF THE INVENTION

In the configuration of the comparator disclosed in Japanese Unexamined Patent Application, First Publication No. 2005-311487, the area of the CMOS image sensor (semiconductor device) increases.

Figure 1:
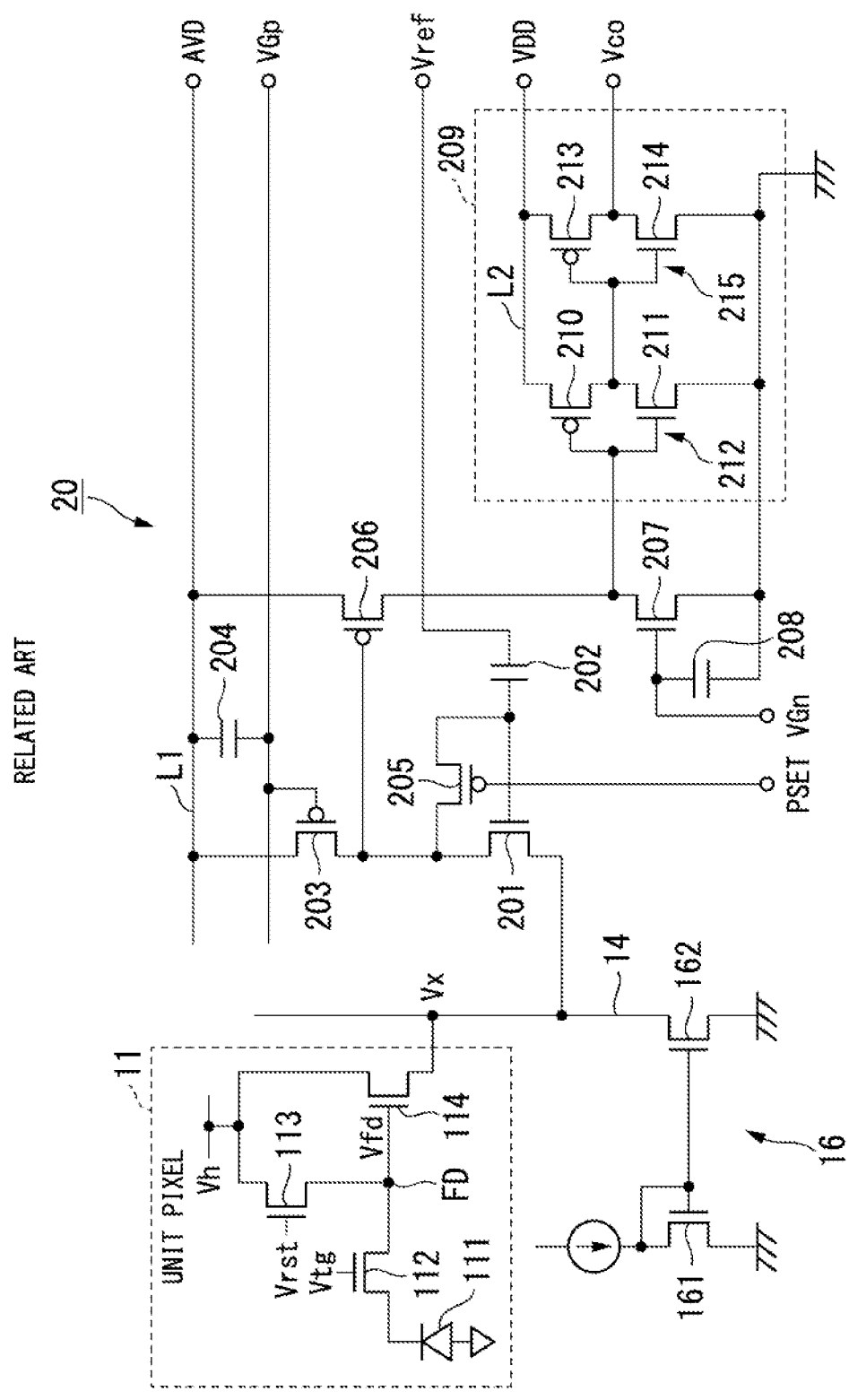
FIG. 1 is a circuit diagram showing a circuit configuration of a comparator in a CMOS image sensor using a column ADC disclosed in Japanese Unexamined Patent Application. First Publication No. 2005-311487.

FIG. 1 is a circuit diagram showing a circuit configuration of the comparator in the CMOS image sensor using the column ADC disclosed in Japanese Unexamined Patent Application. First Publication No. 2005-311487. The comparator used for the conventional column ADC shown in FIG. 1 needs on the column side at least five transistors (an N-channel (Nch) MOS transistor 201, a P-channel (Pch) load MOS transistor 203, a Pch MOS switch (transistor) 205, a Pch MOS transistor 206, and an Nch MOS transistor 207) and one capacitor (a capacitor 202) for canceling offset. In particular, the area of the capacitor 202 for canceling the offset requires a certain amount of layout area that cannot be ignored and the area of the comparator increases. In contrast, the column itself can be minimized by removing the capacitor 202 from the comparator used for the conventional column ADC shown in FIG. 1. However, the imaging device itself becomes complicated and the area of the imaging device increases since a circuit is necessary to supply a circuit that generates a comparison voltage Vref with a higher voltage than a power source voltage Vh.

Figure 2:
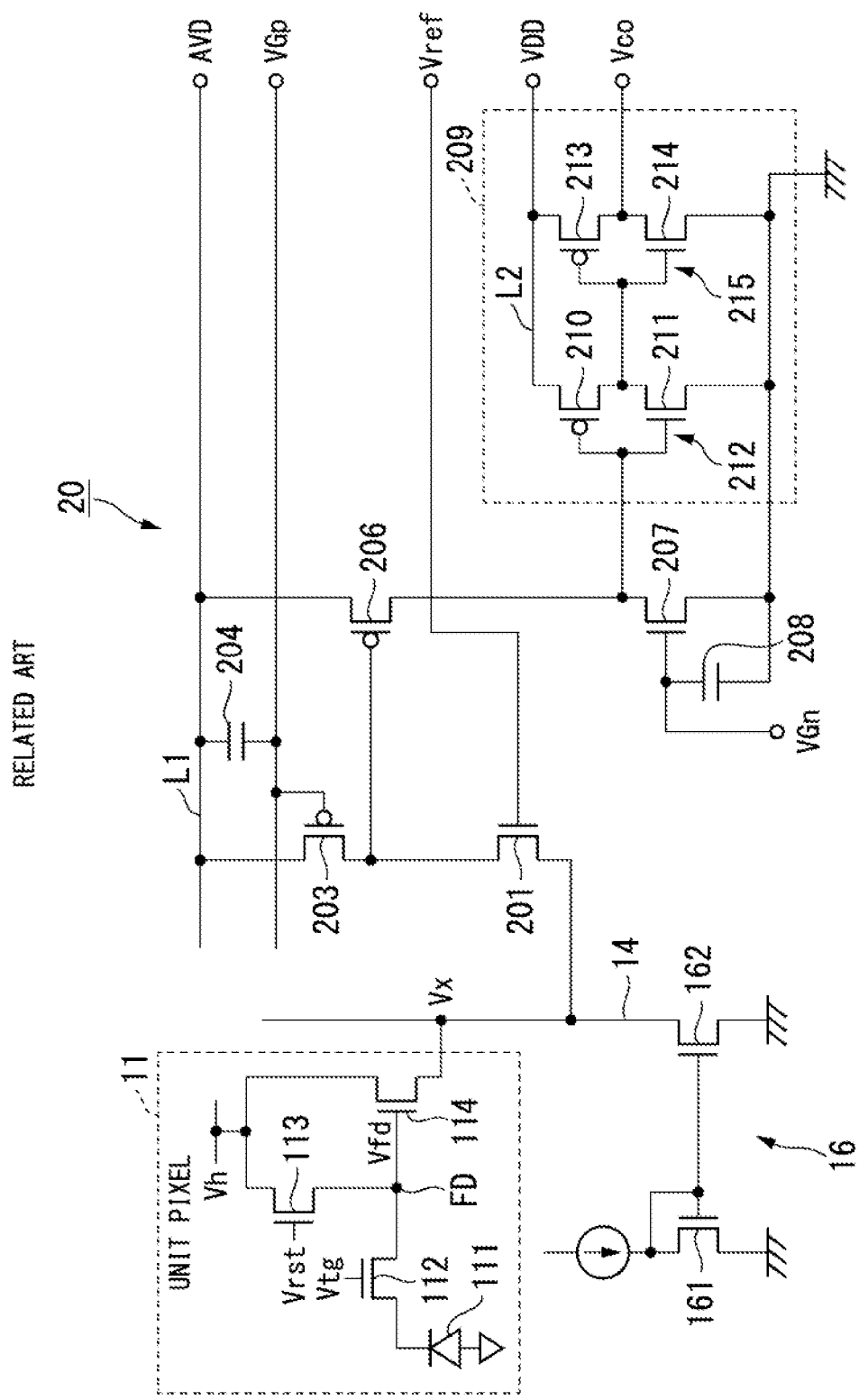
FIG. 2 is a circuit diagram in which a capacitor 202 and a switch 205 are deleted from the comparator used for the column ADC shown in FIG. 1.

FIG. 2 is a circuit diagram in which the capacitor 202 and the switch 205 are deleted from the comparator used for the column ADC shown in FIG. 1. For example, as shown in FIG. 2, in a case in which the capacitor 202 and the switch 205 shown in FIG. 1 are deleted and the influence of clock feed-through is ignored, output of the comparator used for the conventional column ADC is inverted when Vfd and Vref match each other.

Since the maximum voltage that Vfd can take is Vh, a comparison-voltage generation circuit capable of outputting Vref at least greater than Vh for inverting the comparator is necessary in light of the variation (production tolerance of transistors) in the threshold voltage of the transistor 114 and the transistor 201. In general, the variation in the threshold voltage corresponding to the production tolerance of transistors ranges from several tens of mV to several hundred mV. Therefore, in general, a means for supplying a voltage greater than Vh by several hundred mV is necessary at the time of designing a comparison-voltage generation circuit capable of outputting Vref greater than Vh in light of the tolerance.

First Embodiment

Figure 3:
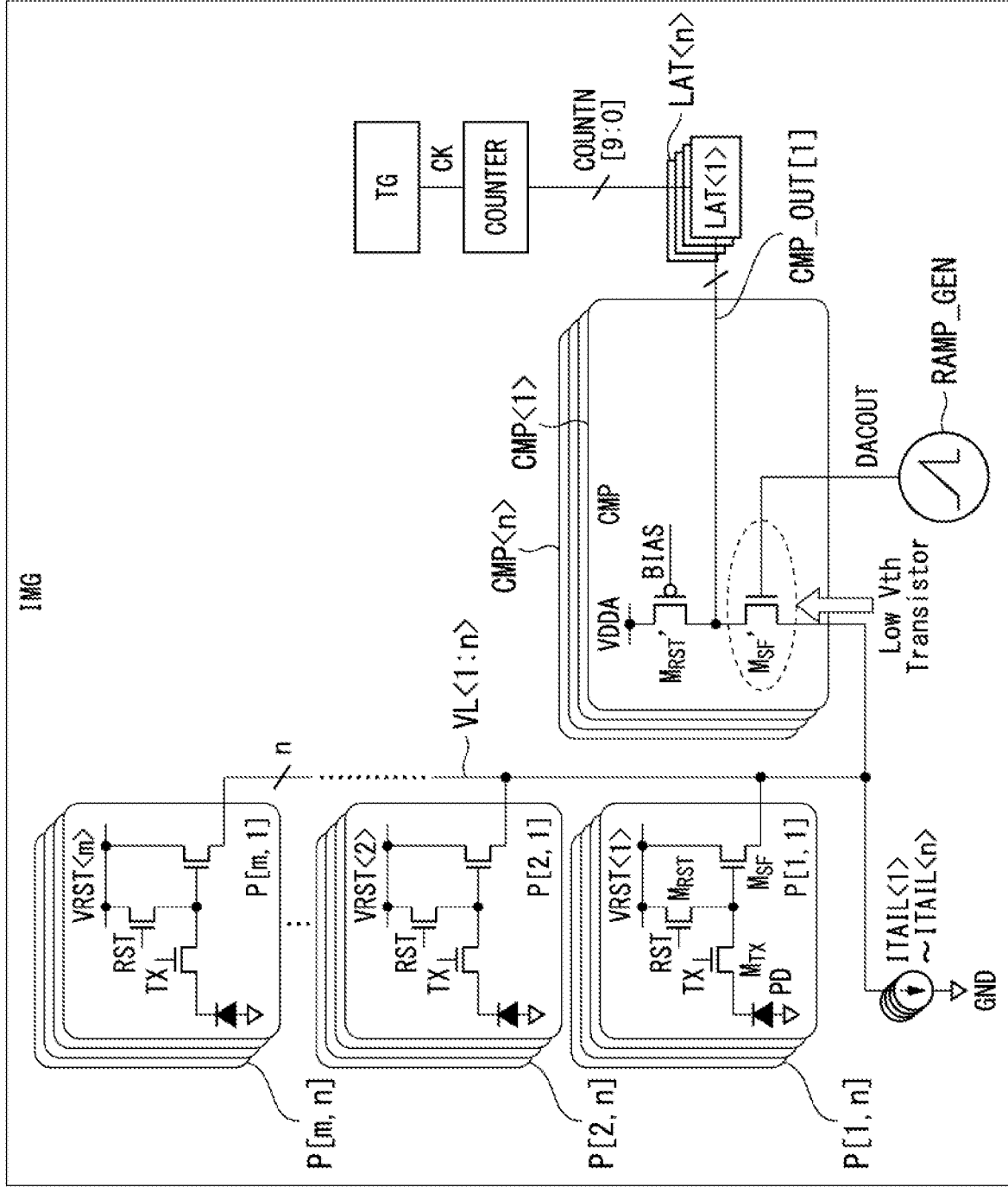
FIG. 3 is a block diagram showing an example of a configuration of an image sensor IMG according to a first embodiment of the present invention.

Hereinafter, a first embodiment of the present invention will be described with reference to the drawings. FIG. 3 is a block diagram showing an example of a configuration of an image sensor IMG according to the first embodiment of the present invention.

<Configuration of Image Sensor IMG>

The image sensor IMG (semiconductor device) shown in FIG. 3 includes m×n pixels P (P[1, 1] to P[m, n]), a timing generator TG, n comparators CMP (CMP<1> to CMP<n>), a ramp-wave generator RAMP_GEN (comparison-voltage generation circuit), n latches LAT (LAT<1> to LAT<n>), a grey-code counter COUNTER, and n tail current sources ITAIL (ITAIL<1> to ITAIL<n>).

In FIG. 3, m×n unit pixels P, each including a photoelectric conversion element, are two-dimensionally arranged in a matrix shape and constitute a plurality of pixel arrays (element arrays). Hereinafter, the unit pixel P is simply called a pixel. In this pixel array, row-control signal lines VRST (VRST<1>, VRST<2>, ..., and VRST<m>) are arranged for each row in the matrix-shaped array of the pixels P, column signal lines (vertical signal lines) Vt. (VL<1>, VL<2>, ... and VL<n>) are arranged for each column in the matrix-shaped array of the pixels P, and each pixel P in the pixel array is connected to one of the column signal lines VL. An address is given to each of the pixels P and the address of each pixel P is different or distinguished from the addresses of the other pixels P. Each pixel P can be selected by designating the address given to the pixel P.

The pixel P includes, for example, a photodiode PD, which is a photoelectric conversion element, and three transistors, namely a transfer transistor $M_{TX}$, a reset transistor $M_{RST}$, and an amplification transistor $M_{SF}$. The source of the amplification transistor $M_{SF}$ is connected to the column signal line $V_L$.

Here, one end of each of the row-control signal lines VRST is connected to the output end of each stage of a row-scanning circuit not shown in the drawing.

The row-scanning circuit is constituted by a sift resistor and the like and executes control of row addresses and row-scanning by sequentially outputting row-selection pulses to the row-control signal lines VRST (VRST<1>. VRST<2>, ..., and VRST<m>). In this way, n pixels P of one row connected to the row-control signal line VRST (VRST<1>, VRST<2>, ..., and VRST<m>) to which the row-selection pulse is applied are selected. A reset signal is output at the time (P (preset) period) of the reset operation and a pixel signal is output at the time (D (data) phase period) of the reading operation (transfer operation) from each pixel P of the selected row to the column signal line VL (VL<1>, VL<2>, ..., and VL<n>). The reset signal is a signal having an analog value that is output when a reset voltage VRST is applied to the amplification transistor $M_{ST}$. The pixel signal is a signal having an analog value that is output when a video voltage VSIG is applied to the amplification transistor $M_{SF}$.

Each of the tail current sources ITAIL<1> to ITAIL<n> is connected to one end of the column signal line VL (VL<1>, VL<2> . . . , and VL<n>). The tail current source ITAIL includes a current-mirror circuit not shown in FIG. 3. The current-mirror circuit includes a first Nch MOS transistor and a second Nch MOS transistor. For example, the gate and the drain of the first Nch MOS transistor are connected to each other and the source of the first Nch MOS transistor is connected to the ground. For example, the gate of the second Nch MOS transistor is connected to the gate of the first Nch MOS transistor, the drain of the second Nch MOS transistor is connected to the column signal line VL, and the source of the second Nch MOS transistor is connected to the ground. The second Nch MOS transistor of this tail current source ITAIL and the amplification transistor $M_{SF}$ of the pixel P form a source follower circuit.

A signal-processing circuit includes the tail current source ITAIL (ITAIL<1> to ITAIL<n>), the comparator CMP (CMP<1> to CMP<n>), and the latch LAT (LAT<1> to LAT<n>). Hereinafter, the signal-processing circuit may be simply called a column circuit.

The comparators CMP (CMP<1> to CMP<n>) are provided at one end of the column signal lines VL (VL<1>, VL<2>, . . . , and VL<n>) so as to correspond to the respective column signal lines VL<1>. VL<2>, . . . , and VL<n>.

In addition, the ramp-wave generator RAMP_GEN, which is a means for generating a reference voltage DACOUT (comparison voltage), the grey-code counter COUNTER, and the timing generator TG are provided in common with the comparators CMP (CMP<1> to CMP<n>).

The ramp-wave generator RAMP_GEN generates the reference voltage DACOUT (comparison voltage) and outputs the reference voltage DACOUT to the comparators CMP (CMP<1> to CMP<n>). The waveform of the reference voltage DACOUT forms a ramp shape in which the level changes in a slope shape as time passes, that is, the level gradually increases or decreases. In the embodiment, since the reference voltage DACOUT is input as a gate voltage of an NMOS transistor, the system in which the level gradually increases from the L level to the H level is used. However, in a case in which the reference voltage DACOUT is input as a gate voltage of a PMOS transistor, in other words, the differential amplification circuit formed by the amplification transistor $M_{SF}$, a pair transistor $M_{SF}'$ constituting the comparator CMP, and the tail current source ITAIL is configured as a differential amplification circuit of the PMOS-input type, the system in which the level gradually decreases from the H level to the L level may be used.

The grey-code counter COUNTER performs a counting operation in synchronization with a clock CK having a predetermined cycle, thus measuring the length of time required for a logic level output by the comparator CMP (CMP<1> to CMP<n>) to be inverted.

The timing generator TG generates the clock CK, which is a standard for the operation of the grey-code counter COUNTER, on the basis of a master clock and provides the grey-code counter COUNTER with the clock CK.

The comparator CMP (CMP<1>, CMP<2>, . . . , and CMP<n>) compares the reference voltage DACOUT (comparison voltage) having a ramp shape generated by the ramp-wave generator RAMP_GIEN with an analog voltage. The amplification transistor $M_{SF}$ in n pixels P selected for each row-control signal line VRST (VRST<1>, VRST<2>, . . . , and VRST<n>) outputs an analog value to the column signal line VL (VL<1>, VL<2>, . . . , and VL<n>) on the basis of the analog voltage (the gate voltage of the amplification transistor $M_{SF}$) compared with the reference voltage DACOUT. The comparator CMP (CMP<1>, CMP<2>, . . . , and CMP<n>) outputs determination signals CMP_OUT[1] to CMP_OUT[n] to the latches LAT (LAT<1>, LAT<2>, . . . , LAT<n>).

The latches LAT (LAT<1>, LAT<2>, . . . , LAT<n>) records or holds information at a predetermined time point described later at which the determination signals CMP_OUT[1] to CMP_OUT[n] change from H to L. The information is included in the counting results acquired in respective comparators CMP (CMP<1>, CMP<2>, . . . , and CMP<n>) by using the grey-code counter COUNTER. The information includes counting data COUNT[9: 0] of p (p=10) bits and also includes the time point of change of the determination signals or a comparison time (a period of time required for comparison and determination) from the time point of starting counting to the time point of change of the determination signals.

In FIG. 3, at the input stage of the comparator CMP, an Nch MOS transistor $M_{SF}'$ of which the source is connected to the column signal line VL is provided. In addition, the MOS transistor $M_{SF}'$ forms a differential pair with the amplification transistor $M_{SF}$ of the pixel P by connecting the source of the MOS transistor $M_{SF}'$ and the source of the amplification transistor $M_{SF}$ together by the column signal line VL. In other words, the amplification transistor $M_{SF}$ constituting the pixel P forms a differential amplification circuit with the pair transistor $M_{SF}'$ (differential transistor) constituting the comparator CMP and the tail current source ITAIL.

The reference voltage DACOUT having a ramp shape generated by the ramp-wave generator RAMP_GEN is applied to the gate of the pair transistor $M_{SF}'$. The drain of the pair transistor $M_{SF}'$ is connected to the drain of the Pch load MOS transistor (active load) $M_{RST}'$ and is connected to the power source line of a voltage VDDA, which is the source of the load MOS transistor $M_{RST}'$, via the load MOS transistor $M_{RST}'$. A DC gate voltage BIAS is applied to the gate of the load MOS transistor $M_{RST}'$. Here, in the first embodiment, the level of the DC gate voltage BIAS is a fixed level when the load MOS transistor (active load) $M_{RST}'$ causes the current that is half the current of the tail current source ITAIL to flow in the drain of the pair transistor $M_{SF}'$.

The drain of the load MOS transistor $M_{RST}'$ and the drain of the pair transistor $M_{SF}'$ are connected together and generate output of the differential amplification circuit including the above-described configuration.

The output of the differential amplification circuit output from the drain of the pair transistor $M_{SF}'$ is a determination signal CMP_OUT[1] (CMP_OUT[1] to CMP_OUT[n]) and a period of time required for the output to be inverted is held in the latch LAT (LAT<1> to LAT<n>) at the next stage. The period of time is indicated by the counting value of the grey-code counter COUNTER at a timing at which the determination signal CMP_OUT[1] (CMP_OUT[1] to CMP_OUT[n]) is inverted.

<Operation of Image Sensor IMG>

As described above, the amplification transistor $M_{SF}$ constituting the pixel P of the first column forms the differential amplification circuit with the pair transistor $M_{SF}'$ constituting the comparator CMP and the tail current source ITAIL<1>. Here, in design, the threshold voltage (voltage threshold) $V_{TH}$ of the pair transistor $M_{SF}'$ is lower than the threshold voltage $V_{TH}$ of the amplification transistor $M_{SF}$ by $\Delta V$. Adjustment of the threshold voltage can be realized by adjusting the ion concentration of a transistor.

Such a transistor is known as a low-Vtn transistor and is provided on the assembly line of general semiconductor manufacturers. It is known that the threshold voltage $V_{TH}$ of a semiconductor transistor is generally given by the following expression. The relative threshold voltage can be reduced by increasing the value of the intrinsic carrier concentration ni of the pair transistor $M_{SF}'$ with respect to the amplification transistor $M_{SF}$.

$$V_{TH}=\Phi_{MS}+2\Phi_F+Q_{dep}/C_{ox}$$

Here, $\Phi_{MS}$ is the difference between the work functions of the poly-gate and silicon, and $\Phi_F$ is the Fermi level given by the following expression.

$$\Phi_F=(kT/q)\ln(N_{sub}/n_i)$$

Here, k is the Boltzmann constant, T is the absolute temperature, q is the amount of charge of an electron, $N_{sub}$ is the impurity concentration of a substrate, and $n_i$ is the intrinsic carrier concentration.

In addition, $Q_{dep}$ is a value (amount of charge at the interface of a depletion layer) given by the following expression.

$$Q_{dep}=(4q\varepsilon_{S1}|\Phi_F|N_{sub})^{1/2}$$

Here, $\varepsilon_{S1}$ is the dielectric constant of silicon.

In addition, $C_{ox}$ is the capacitance value of a gate oxide film per unit area.

Therefore, by using the low-$V_{TH}$ transistor as the pair transistor $M_{SF}'$, it is possible to realize the comparator CMP<1> including the differential pair formed by the amplification transistor $M_{SF}$ and the pair transistor $M_{SF}'$ that is turned on at a lower voltage than the voltage of the amplification transistor $M_{SF}$ by ΔV. Thus, a column-parallel type image sensor can be realized without providing a capacitor for canceling offset and a boosting circuit for the ramp-wave generator, and the chip area can be miniaturized.

In other words, the above-described differential amplification circuit inverts its output (the drain voltage of the pair transistor $M_{SF}'$ that is the output of the differential amplification circuit) when the condition indicated as "$V_{SF}=V_{SF}'+\Delta V$" is met. Here, $V_{SF}$ and $V_{SF}'$ are the gate voltage of the amplification transistor $M_{SF}$ and the pair transistor $M_{SF}'$, respectively. That is, at the moment the voltage difference between $V_{SF}'$ and $V_{SF}$ becomes less than ΔV, the determination signal CMP_OUT (CMP_OUT[1], CMP_OUT[2], . . . . CMP_OUT[n]), which is the output signal of the comparator CMP (CMP<1>, CMP<2>, . . . and CMP<n>), changes from H to L. Here, ΔV is set such that the condition indicated as "ΔV=(the threshold voltage of the amplification transistor $M_{SF}$)−(the threshold voltage of the pair transistor $M_{SF}'$)>0" is met as described above when designing the image sensor IMG However, in the produced image sensor IMG the threshold voltage (characteristic value) of the amplification transistor $M_{SF}$ has variation ΔV (measured value) of the threshold voltage due to the variation at the time of production. The absolute value of the above-described ΔV (designed value) is designed so as to be greater than the absolute value of ΔV (measured value). The measured value of the threshold voltage indicates an actual value of the threshold voltage.

The above is described in more detail below. In a case in which the relative threshold voltage of the amplification transistor $M_{SF}$ with respect to the threshold voltage of the pair transistor $M_{SF}'$ increases due to the variation of the threshold voltage, ΔV (measured value) increases. In other words, when the threshold voltage Vt of the amplification transistor $M_{SF}$ is the maximum value Vtmax, the threshold voltage Vt of the pair transistor $M_{SF}'$ is less than the threshold voltage Vtmax of the amplification transistor $M_{SF}$ and therefore the condition indicated as "(the maximum value of ΔV (measured value) on the positive side)=(the threshold voltage Vtmax of the amplification transistor $M_{SF}$)−(the threshold voltage Vt of the pair transistor $M_{SF}'$) (>0)" is met.

On the other hand, when the threshold voltage of the amplification transistor $M_{SF}$ with respect to the threshold voltage of the pair transistor $M_{SF}'$ decreases due to the variation of the threshold voltage, ΔV (measured value) decreases in some cases, reaches zero in other cases ((the threshold voltage Vt of the pair transistor $M_{SF}'$)=(the threshold voltage Vt of the amplification transistor $M_{SF}$)), and further reaches a negative value in the other cases. In other words, when the threshold voltage Vt of the amplification transistor $M_{SF}$ is the minimum value Vtmin, the threshold voltage Vt of the pair transistor $M_{SF}'$ is greater than the threshold voltage Vtmin of the amplification transistor $M_{SF}$ and therefore the condition indicated as "(the maximum value of ΔV (measured value) on the negative side)=(the threshold voltage Vtmin of the amplification transistor $M_{SF}$)−(the threshold voltage Vt of the pair transistor $M_{SF}'$) (<0)" is met.

Thus, the two maximum values of positive and negative ΔV (measured value) are called "maximum values of variation" and the comparator CMP inverts the output of the determination signal CMP_OUT output from the comparator CMP when the condition indicated as "$V_{SF}+\Delta V$ (measured value)=$V_{SF}'+\Delta V$ (designed value)" is met. Here, $V_{SF}$ and $V_{SF}'$ are the gate voltage of the amplification transistor $M_{SF}$ and the pair transistor $M_{SF}'$, respectively. According to the above, since the condition indicated as "$V_{SF}=V_{SF}'+(\Delta V$ (designed value)−ΔV (measured value))" and the condition indicated as "(ΔV (designed value)−ΔV (measured value))>0" are met, the output of the determination signal CMP_OUT is inverted at the moment the difference between $V_{SF}$ and $V_{SF}'$ matches "ΔV (designed value)−ΔV (measured value)."

In other words, the comparator CMP compares a first analog signal (voltage of a pixel) input to one end of an input terminal with a comparison-voltage signal (voltage generated by a comparison-voltage generation circuit) input to the other end of the input terminal, in other words, compares the first analog signal output from the element array to which addresses are given with the comparison voltage generated by the comparison-voltage generation circuit. It is guaranteed that the output of the determination signal CMP_OUT is inverted at a timing at which the comparison voltage and the value of a second analog signal generated by adding a predetermined absolute value to the first analog signal match each other. Therefore, a small semiconductor device can be provided without providing a capacitor for canceling offset and a boosting circuit for generating the comparison voltage even when the variation is present in the threshold voltage Vt of the amplification transistor $M_{SF}$. The predetermined absolute value is, for example, greater than or equal to 30 mV and less than or equal to 500 mV.

Hereinafter, the above-described ΔV (measured value) is used as ΔV.

In other words, the comparator CMP (CMP<1> to CMP<n>) in the signal-processing circuit includes the pair transistor (differential transistor) $M_{SF}'$ constituting a differential pair with the amplification transistor $M_{SF}$ of the pixel array when the pixel array (element array) to which an address is given and the signal-processing circuit are connected together by the column signal line (vertical signal lines) VL(VL<1>, VL<2>, . . . , and VL<n>). The comparator CMP acquires the difference between the reference voltage (comparison voltage) DACOUT ($V_{SF}'$) input to the pair transistor $M_{SF}'$ of the signal-processing circuit and the analog voltage ($V_{SF}$) input to the amplification transistor $M_{SF}$ of the pixel array. The comparator CMP_OUT outputs "H (high)" level as the determination signal CMP_OUT when the condition indicated as "$V_{SF}-V_{SF}'=\Delta V>0$" is met and outputs "L (low)" level as the determination signal CMP_OUT when the condition indicated as "$V_{SF}-V_{SF}'=\Delta V<0$" is met.

In addition, the latch (storage circuit) LAT (LAT<1> to LAT<n>) in the signal-processing circuit stores n timings at which the difference $\Delta V$ (the difference between the reference voltage DACOUT and the analog voltage) matches the predetermined absolute value greater than the maximum value of variation in the threshold voltage of the amplification transistor $M_{SF}$ of the pixel array.

Figure 4:
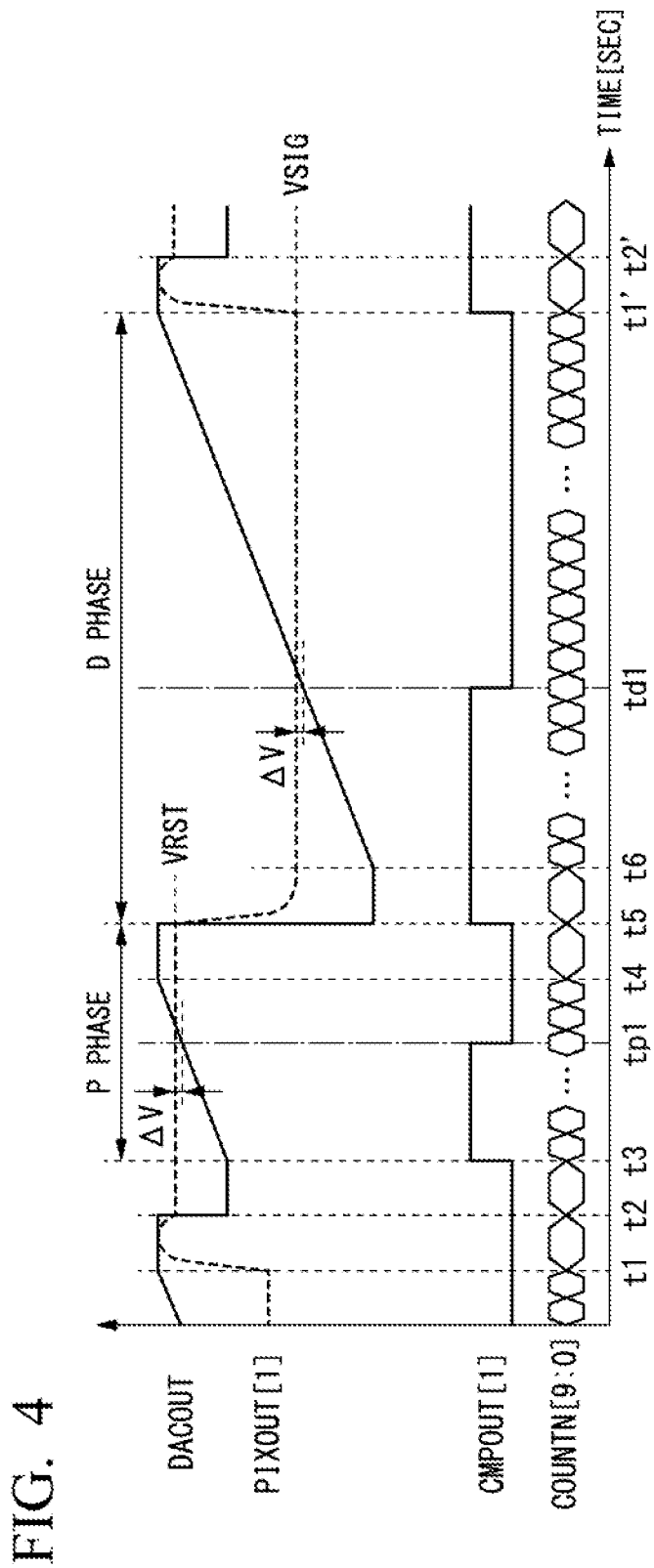
FIG. 4 is a timing chart showing an operation of the image sensor IMG according to the first embodiment of the present invention.

Next, an operation of the image sensor IMG will be described by using FIG. 4. FIG. 4 is a timing chart showing an operation of the image sensor IMG according to the embodiment.

The horizontal axis of the timing chart shown in FIG. 4 indicates time [sec] and the vertical axis of the timing chart indicates the change in level of the reference voltage DACOUT input to the amplification transistor $M_{SF}$, the analog voltage PiXOUT[1] input as a gate voltage of the pair transistor $M_{SF}'$ (differential transistor) in the comparator CMP<1>, the determination signal CMP_OUT[1] of the comparator CMP<1>, and the counting data COUNT[9:0] counted by the grey-code counter COUNTER at each time point as main signals in the image sensor IMG The image sensor IMG outputs the determination signal CMP_OUT[1] by using the comparator CMP<1> when a reset signal is output from the pixel P[1, 1] selected by using the mw-control signal line VRST<1> to the column signal line VL<1> in a period of the P phase indicated by the time points t3 to t5 in accordance with the timing chart shown in FIG. 4. The reset signal is a signal having an analog value when the reset voltage VRST is applied to the amplification transistor $M_{SF}$. In addition, the image sensor IMG outputs the determination signal CMP_OUT[1] by using the comparator CMP<1> when a pixel signal is output from the pixel P[1] selected by using the row-control signal line VRST<1> to the column signal line VL<1> in a period of the D phase indicated by the time points t5 to t1' in accordance with the timing chart shown in FIG. 4. The pixel signal is a signal having an analog value when the video voltage VSIG is applied to the amplification transistor $M_{SF}$.

First, the pixel P[1, 1] is reset when the reset transistor $M_{RST}$ is turned on at the time point t1 and the reset voltage VRST appears at the gate of the amplification transistor $M_{SF}$ when the reset transistor $M_{RST}$ is turned off at the time point t2. The ramp-wave generator RAMP_GEN starts generating the ramp wave (DACOUT) at the time point 3 and, at the same time, the grey-code counter COUNTER starts counting the counting data COUNTN[9: 0]. Thereafter, the ramp wave continues to rise, the counting continues to be performed, and the determination signal CMP_OUT[1] of the comparator CMP<1> changes from H to L at the time point tp1. This is because the gate voltage $V_{SF}$ (=VRST) of the amplification transistor $M_{SF}$ constituting the differential amplification circuit and the gate voltage $V_{SF}'$ (=DACOUT) of the pair transistor $M_{SF}'$ (differential transistor) forming the differential pair with the amplification transistor $M_{SF}$ meet the condition indicated as "$V_{SF}=V_{SF}'+\Delta V$" and the drain voltage of the pair transistor $M_{SF}'$ that is the output of the differential amplification circuit is inverted. In addition, the latch LAT<1> holds the value of the counting data COUNTN [9: 0] at the time point tp1. This counting continues until the time point t4 and timings at which the determination signals CMP_OUT[1] to CMP_OUT[n] of all the columns are inverted before the time point t4 are recorded in the latches LAT<1> to LAT<n>, each being provided for each column.

Next, at the time point t5, the transfer transistor $M_{TX}$ in the pixel is turned on and the video voltage VSIG appears at the gate of the amplification transistor $M_{SF}$. The ramp-wave generator RAMP_GEN starts generating the ramp wave (DACOUT) at the time point t6 and, at the same time, the grey-code counter COUNTER starts counting the counting data COUNTN[9: 0]. Thereafter, the ramp wave continues to rise, the counting continues to be performed, and the determination signal CMP_OUT[1] of the comparator CMP<1> changes from H to L at the time point td1. This is because the gate voltage $V_{SF}$ (=VSIG) of the amplification transistor $M_{SF}$ constituting the differential amplification circuit and the gate voltage $V_{SF}'$ (=DACOUT) of the pair transistor $M_{SF}'$ (differential transistor) forming the differential pair with the amplification transistor $M_{SF}$ meet the condition indicated as "$V_{SF}=V_{SF}'+\Delta V$ (measured value)" and the drain voltage of the pair transistor $M_{SF}'$ that is the output of the differential amplification circuit is inverted. In addition, the latch LAT<1> holds the value of the counting data COUNTN[9: 0] at the time point td1. This counting continues until the time point t1' and timings at which the determination signals CMP_OUT[1] to CMP_OUT[n] of all the columns are inverted before the time point t1' are recorded in the latches LAT<1> to LAT<n>, each being provided for each column.

Pieces of information of the latches LAT<1> to LAT<n> in which the timings of the time point tp1 and the time point td1 at which the signal is inverted are output to the outside of the image sensor IMG in turn by a signal transmission means not shown in the drawing.

As described above, by using the comparator CMP (CMP<1> to CMP<n>) including the differential pair formed by the amplification transistor $M_{SF}$ and the pair transistor $M_{SF}'$ that is turned on at the voltage lower than the voltage at which the amplification transistor $M_{SF}$ is turned on by $\Delta V$, the column-parallel type image sensor IMG can be realized without providing a capacitor for canceling offset and a boosting circuit for the ramp-wave generator. Therefore, the chip area can be miniaturized.

First Modified Example of First Embodiment

Figure 5:
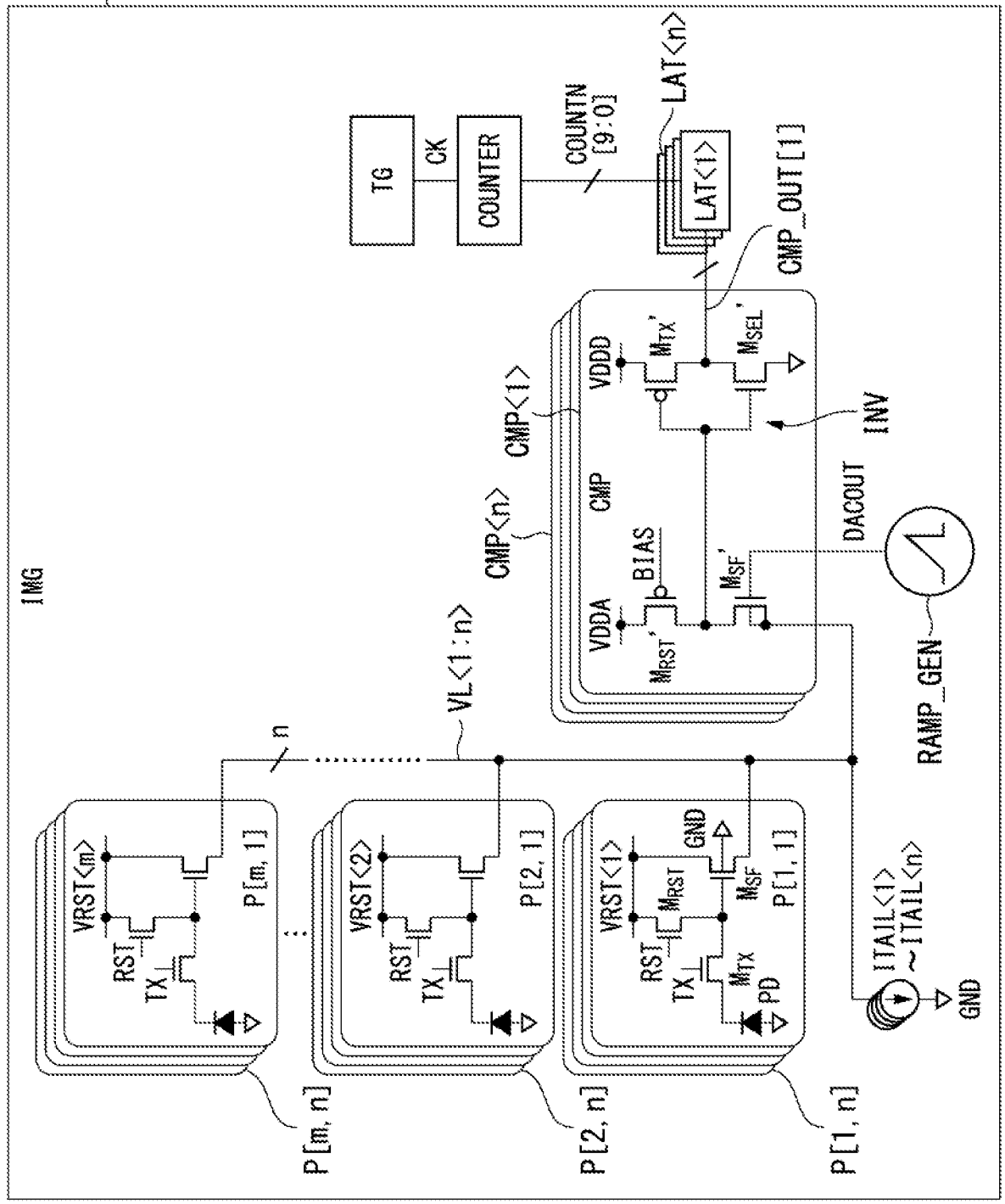
FIG. 5 is a diagram showing an example of a configuration of an image sensor IMG1 according to a first modified example of the first embodiment of the present invention.

Next, a first modified example of the first embodiment of the present invention will be described with reference to the drawings. FIG. 5 is a diagram showing an example of a configuration of an image sensor IMG1 according to the first modified example of the first embodiment of the present invention. In FIG. 5, the same reference numerals are given or the reference signs including characters and the same numbers are given to the same or corresponding configuration shown in FIG. 3 and a description is omitted accordingly.

As shown in FIG. 5, the back gate terminal of the amplification transistor $M_{SF}$ may be biased at GND (ground) and the back gate terminal of the pair transistor $M_{SF}'$ may be connected to the same voltage as that of the source terminal thereof or may be connected (self-biased) to the source terminal thereof.

The reason of that is as follows. The threshold voltage $V_{TH}$ of the amplification transistor $M_{SF}$ in light of the substrate bias effect is given by the following expression. As shown in the expression, the threshold voltage is the smallest when the back gate of the transistor is self-biased, and the threshold voltage increases as the difference between the voltage of the back gate of the transistor and the voltage of the source of the transistor increases. Here. $V_{SB}$ is the voltage between the source and back gate of the transistor and γ is a predetermined coefficient called a threshold voltage parameter.

$$V_{TH}=V_{TH0}+\gamma\{(2\Phi_F+V_{SB})^{1/2}-(2\Phi_F)^{1/2}\}$$

On the other hand, the threshold voltage $V_{TH}$ of the amplification transistor $M_{SF}$ is given by the following expression obtained by using 0 as $V_{SB}$ in the above-described expression.

$$V_{TH}=V_{TH0}+\gamma\{(2\Phi_F)^{1/2}-(2\Phi_F)^{1/2}\}$$

In other words, the threshold voltage $V_{TH}$ of the amplification transistor $M_{SF}$ decreases by the amount in accordance with the influence by the term of the variation $V_{SB}$ of the threshold voltage due to the substrate bias effect.

Thus, in the image sensor IMG1 shown in FIG. 5, the back gate terminal of the pair transistor $M_{SF}'$ (differential transistor) of the column circuit is biased to the same voltage as that of the source terminal of the pair transistor $M_{SF}'$ and the back gate terminal of the amplification transistor $M_{SF}$ of the pixel array (element array) is biased to the voltage lower than that of the source terminal of the pair transistor $M_{SF}'$.

In this way, in design, the threshold voltage of the pair transistor $M_{SF}'$ can be configured to be lower than the threshold voltage of the amplification transistor $M_{SF}$ by ΔV. Therefore, the comparator used for a smaller column circuit than a conventional one can be realized without providing a capacitor and a special power source and the image sensor IMG1 can be miniaturized.

In the comparator CMP (CMP<1> to CMP<n>) according to the embodiment, as shown in FIG. 5, the CMOS inverter constituted by the transistor $M_{TX}'$ and the transistor $M_{SEL}'$ is provided between the drain terminal of the pair transistor $M_{SF}'$ and the latch LAT. The CMOS inverter like this may be included in the comparator CMP provided between the drain terminal of the pair transistor $M_{SF}'$ and the latch LAT.

In addition, in the embodiment, the transistors included in the pixels P[1, 1] to P[m, n], the comparators CMP(CMP<1> to CMP<n>), the ramp-wave generator RAMP_GEN, and the tail current sources ITAIL<1> to ITAIL<n> may be constituted by high voltage-resistant transistors (for example, resistant to 3.6 V with minimum gate length of 330 nm) and the transistors included in the timing generator TC the latches LAT, and the grey-code counter COUNTER may be constituted by low voltage-resistant transistors (for example, resistant to 1.4 V with minimum gate length of 65 nm).

Furthermore, the maximum voltage of the voltage VRST<m> supplied to the pixels P[1. 1] to P[m, n] and the voltage supplied to the reset transistor $M_{RST}$ may be the normal operation voltage (for example, 3.3 V) of the high voltage-resistant transistors and the voltage supplied to the inverter INV (CMOS inverter described above), the latches LAT, the grey-code counter COUNTER, and the timing generator TG may be the normal operation voltage (for example, 1.2 V) of the low voltage-resistant transistors. According to this configuration, by supplying the pixel unit with sufficient operation voltage, advantages of reducing power consumption by using the low voltage-resistant transistors in the digital domain can be obtained and advantages of reducing the area can also be obtained while an adequate S/N ratio can be secured in the analog domain. In a case in which the inverter INV is provided in the embodiment, the logic of the determination signal CMP_OUT (CMP_OUT [1], CMP_OUT[2], . . . , CMP_OUT[n]) in FIG. 4 is inverted, but it should be noted that the basic operation of the entire image sensor IMG1 is not different from the basic operation of the entire image sensor IMG In the embodiment, as a means for connecting the analog voltage domain and the digital voltage domain together, the specific example of the inverter INV constituted by the high voltage-resistant transistors and to which the normal operation voltage of the low voltage-resistant transistors is supplied is described. However, a modified example of a buffer, a level sifter, or the like having similar functions can also be adopted. In a case in which a buffer or a level sifter is used, the logic of the determination signal CMP_OUT in FIG. 4 does not need to be inverted.

Second Modified Example of First Embodiment

Figure 6:
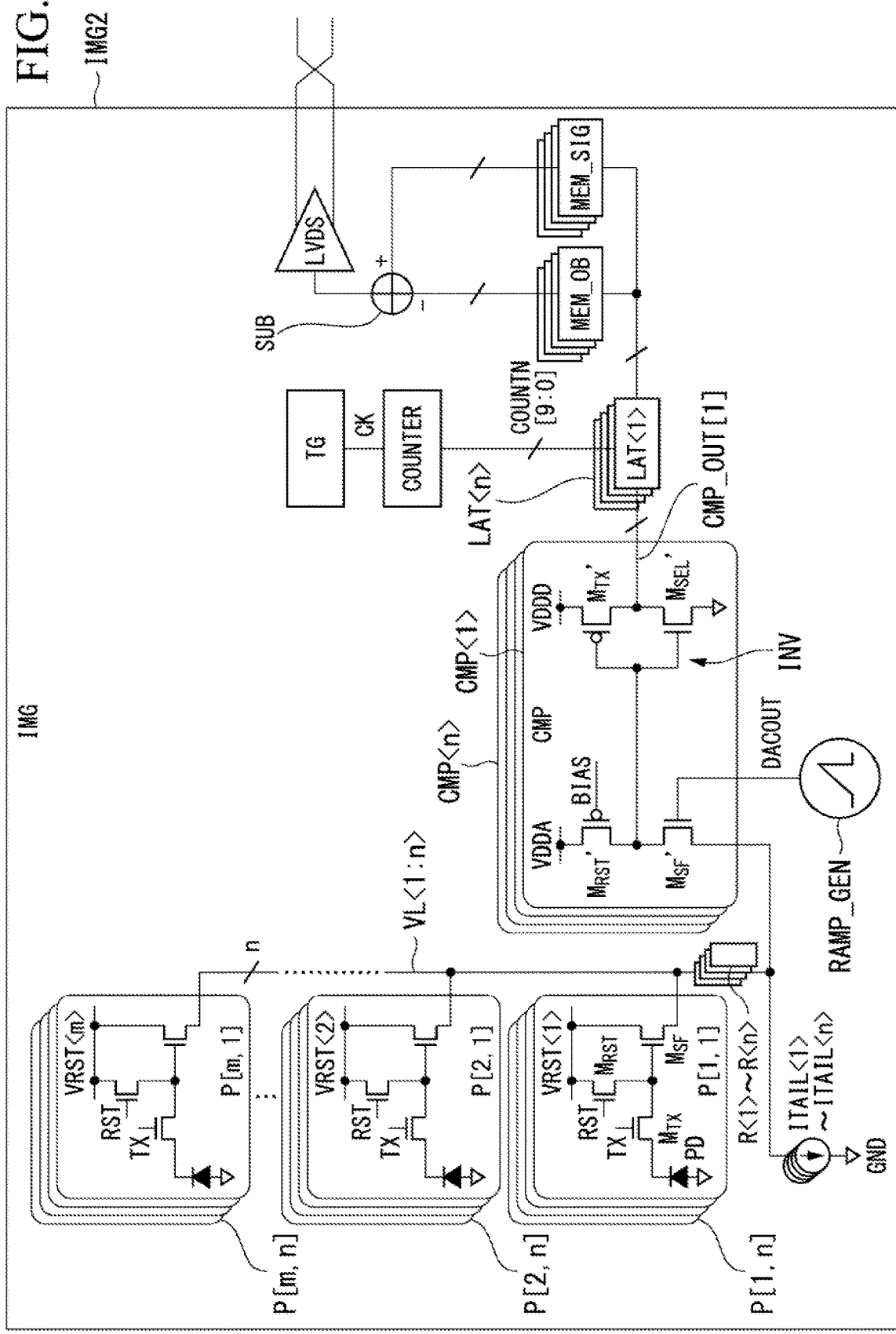
FIG. 6 is a diagram showing an example of a configuration of an image sensor IMG2 according to a second modified example of the first embodiment of the present invention.

Next, a second modified example of the first embodiment of the present invention will be described with reference to the drawings. FIG. 6 is a diagram showing an example of a configuration of an image sensor IMG2 according to the second modified example of the first embodiment of the present invention. In FIG. 6, the same reference numerals are given or the reference signs including characters and the same numbers are given to the same or corresponding configuration shown in FIG. 3 and FIG. 5 and a description is omitted accordingly.

As shown in FIG. 6, resistors R<1> to R<n> may be inserted between the source terminal of the amplification transistor $M_{SF}$ and the tail current sources ITAIL<1> to ITAIL<n>. In general, in a case in which the comparator CMP (CMP<1> to CMP<n>) is designed, the output signal of the comparator CMP (CMP<1> to CMP<n>) is inverted when the voltage input to the amplification transistor $M_{SF}$ constituting the input differential pair matches the voltage input to the pair transistor $M_{SF}'$ constituting the input differential pair. In order to realize this design, the bias current Ibias of the reset transistor $M_{RST}$ is (1/2)Itail.

Even in design of the modified example, the bias current Ibias of the reset transistor $M_{RST}$ is (1/2)Itail. The output of the comparator like this starts to be inverted at a timing at which the gate-source voltage of the amplification transistor $M_{SF}$ matches the gate-source voltage of the pair transistor $M_{SF}'$.

In a case in which the pixel P[1, 1] in the first row and the first column has been selected and the resistance value of the resistor R<1> is 0, the timing at which the output of the comparator starts to be inverted is the moment at which the condition indicated as "Ibias=(1/2)Itail" is met.

In the case of the embodiment (modified example), the source voltage of the amplification transistor $M_{SF}$ increases by the product of the resistance value r1 of the resistor R<1> and the current (Itail−Ibias) flowing in the amplification transistor $M_{SF}$. When the current flowing in the pair transistor $M_{SF}'$ is Ibias, the current flowing in the amplification transistor $M_{SF}$ is (Itail−Ibias) and therefore ΔV in FIG. 6 is r1×(Itail−Ibias)=r1×(1/2)Itail.

In other words, in the image sensor IMG2 shown in FIG. 6, the resistors R<1> to R<n> (level-shift circuit) causing the source voltage of the amplification transistor $M_{SF}$ of the pixel array (element array) to be higher than the source voltage of the pair transistor $M_{SF}'$ of the column circuit are provided between the amplification transistor $M_{SF}$ of the pixel array and the tail current sources ITAIL<1> to ITAIL<n> of the signal-processing circuit.

In this way, in design, the effective threshold voltage of the pair transistor $M_{SF}'$ can be configured to be lower than the threshold voltage of the amplification transistor $M_{SF}$ by ΔV. Therefore, the comparator used for a smaller column circuit than a conventional one can be realized without providing a capacitor and a special power source and the image sensor IMG2 can be miniaturized.

The image sensor IMG2 may include an OB memory MEM_OB that holds the AD-conversion result of OB output, a video memory MEM_SIG that holds the AD-conversion result of video output, a subtractor SUB that performs subtraction using these two values of the AD-conversion results, and a low-voltage differential-signaling (LVDS) driver as shown in FIG. 6.

The OB memories MEM_OB<1> to MEM_OB<n> hold counting data COUNTN[9: 0] (counting data held by each of the latches LAT<1> to LAT<n>) at a timing (time point tp1) at which the comparators CMP (CMP<1> to CMP<n>) cause the determination signals CMP_OUT[1] to CMP_OUT[n] to be inverted regarding the P phase (analog voltage=VRST).

In addition, the video memories MEM_SIG<1> to MFM_SIG<n> hold the counting data COUNTN[9: 0] (counting data held by each of the latches LAT<1> to LAT<n>) at a timing (time point td1) at which the comparators CMP (CMP<1> to CMP<n>) cause the determination signals CMP_OUT[1] to CMP_OUT[n] to be inverted regarding the D phase (analog voltage=VSIG).

In addition, the subtractor SUB subtracts the counting data COUNTN[9: 0] stored on the OB memories MEM_OB<1> to MEM_OB<n> from the counting data COUNTN[9: 0] stored on the respective video memories MEM_SIG<1> to MEM_SIG<n>, thus generating image data.

Furthermore, low-voltage differential signals (LVDS), which are interfaces used for transmitting signals having a small amplitude at high speed, are applied to the LVDS driver and an input signal (image data) is input to the LVDS driver. The LVDS driver converts the input signal into a differential signal that has a signal level ranging from the positive (+) direction to the negative (−) direction and also has the amplitude of, for example, 350 mV and outputs the differential signal to an external device through a pair of output-signal lines (two cables).

By applying the above-described image sensor IMG2 to an endoscope system, the transfer speed of data that the LVDS driver can output can be reduced, and therefore, transmission of video signals by using a thin transmission cable can be realized.

As described above, the image sensor IMG2 can be miniaturized by realizing the comparator used for a smaller column circuit than a conventional one without providing a capacitor and a special power source and also can thin a cable by reducing the transfer rate of video signals. Therefore, the image sensor suitable for use in the endoscope system can be provided.

The point that a cable can be thinned by reducing the transfer rate of video signals when the image sensor is used for the endoscope system will be described in detail after describing a second embodiment of the present invention.

Third Modified Example of First Embodiment

Figure 7:
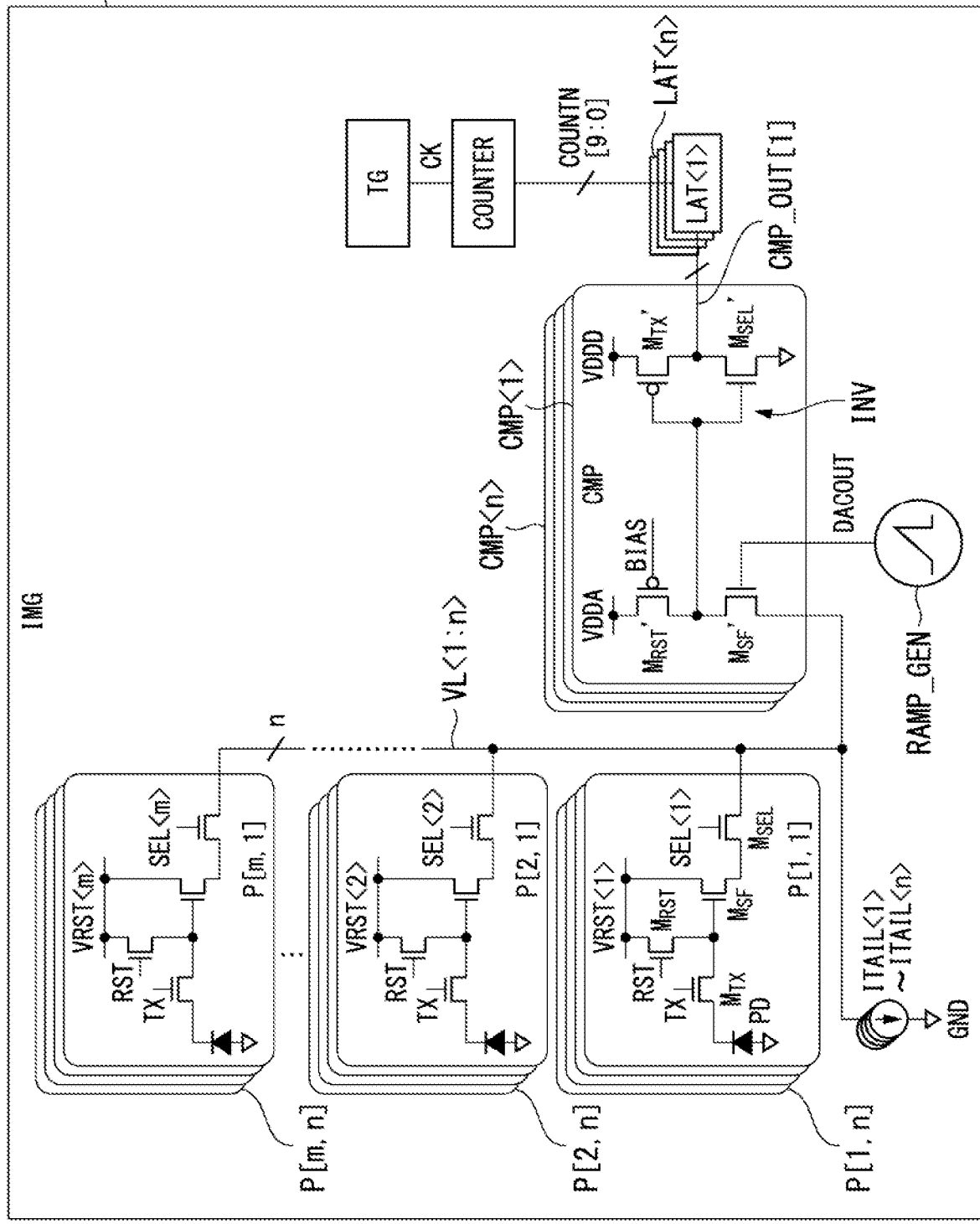
FIG. 7 is a diagram showing an example of a configuration of an image sensor IMG3 according to a third modified example of the first embodiment of the present invention.

Next, a third modified example of the first embodiment of the present invention will be described with reference to the drawings. FIG. 7 is a diagram showing an example of a configuration of an image sensor IMG3 according to the third modified example of the first embodiment of the present invention. In FIG. 7, the same reference numerals are given or the reference signs including characters and the same numbers are given to the same or corresponding configuration shown in FIG. 3, FIG. 5, and FIG. 6 and a description is omitted accordingly.

As shown in FIG. 7, a selection switch $M_{SEL}$ may be inserted between the source terminal of the amplification transistor $M_{SF}$ and the tail current sources ITAIL<1> to ITAIL<n>.

In a case in which the on-resistance of the selection switch $M_{SEL}$ is defined as r2, ΔV in FIG. 7 is expressed as "r2×(Itail−Ibias)" for the same reason as that in the discussion of the second modified example.

In other words, in the image sensor IMG3 shown in FIG. 7, the selection switch $M_{SEL}$ (level-shift circuit) causing the source voltage of the amplification transistor $M_{SF}$ of the pixel array (element array) to be higher than the source voltage of the pair transistor $M_{SF}'$ of the column circuit is provided between the amplification transistor $M_{SF}$ of the pixel array and the tail current sources ITAIL<1> to ITAIL<n> of the signal-processing circuit.

In this way, in design, the threshold voltage of the pair transistor $M_{SF}'$ can be configured to be lower than the threshold voltage of the amplification transistor Msc by ΔV. Therefore, the comparator used for a smaller column circuit than a conventional one can be realized without providing a capacitor and a special power source and the image sensor IMG3 can be miniaturized.

Fourth Modified Example of First Embodiment

Figure 8:
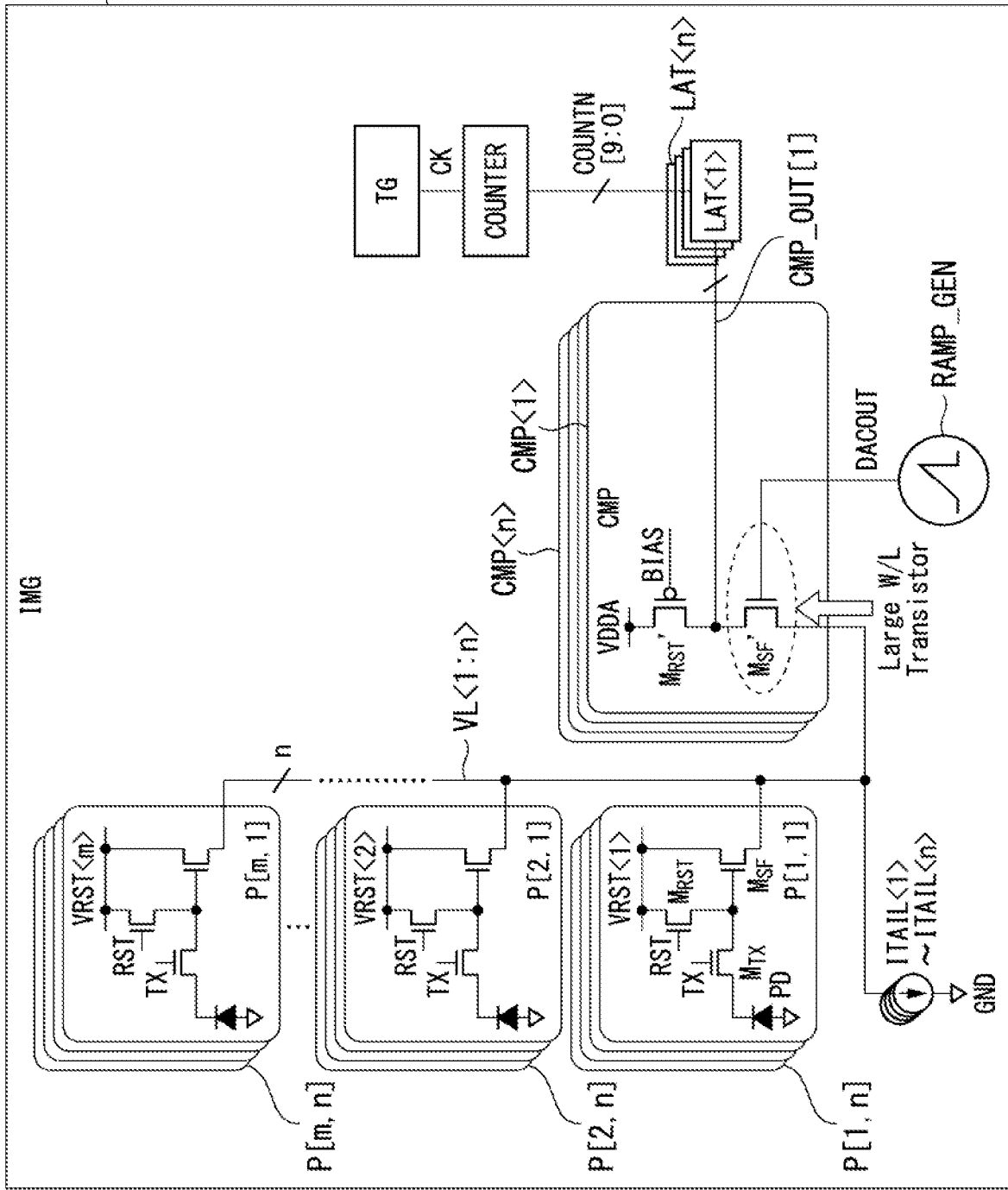
FIG. 8 is a diagram showing an example of a configuration of an image sensor IMG4 according to a fourth modified example of the first embodiment of the present invention.

Next, a fourth modified example of the first embodiment of the present invention will be described with reference to the drawings. FIG. 8 is a diagram showing an example of a configuration of an image sensor IMG4 according to the fourth modified example of the first embodiment of the present invention. In FIG. 8, the same reference numerals are given or the reference signs including characters and the same numbers are given to the same or corresponding configuration shown in FIG. 3. FIG. 5. FIG. 6, and FIG. 7 and a description is omitted accordingly.

As shown in FIG. 8, the aspect ratio of W (channel width)/L (channel length) of the pair transistor $M_{SF}'$ may be set to be greater than the aspect ratio of W/L of the amplification transistor $M_{SF}$. The reason of that is as follows. When the gate-source voltage of one transistor matches the gate-source voltage of the other transistor and the transistors have the same aspect ratio of W/L, the comparator CMP (CMP<1> to CMP<n>) starts inverting its output. The drain current of the transistor to which a predetermined gate-source voltage is given is almost proportional to the aspect ratio. Therefore, the comparator starts inverting its output even when the gate-source voltage of the pair transistor $M_{SF}'$ is lower than the gate-source voltage of the amplification transistor $M_{SF}$.

In other words, in the image sensor IMG4 shown in FIG. 8, the aspect ratio of W/L of the pair transistor $M_{SF}'$ (differential transistor) of the signal-processing circuit is greater than the aspect ratio of W/L of the amplification transistor $M_{SF}$ of the pixel array (element array).

In this way, in design, the threshold voltage of the pair transistor $M_{SF}'$ can be configured to be lower than the threshold voltage of the amplification transistor $M_{SF}$ by ΔV. Therefore, the comparator used for a smaller column circuit than a conventional one can be realized without providing a capacitor and a special power source and the image sensor IMG4 can be miniaturized.

Second Embodiment

Figure 9:
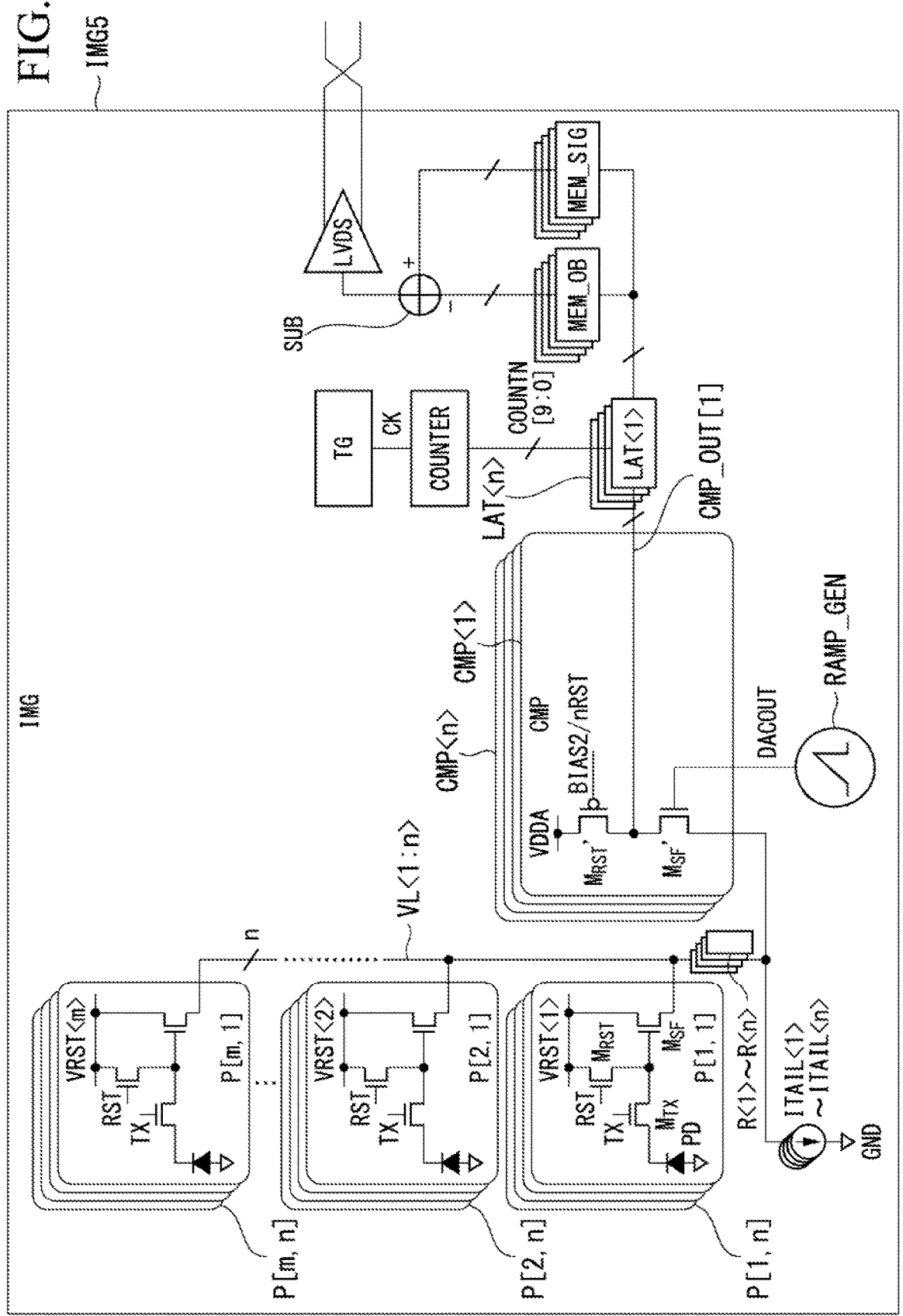
FIG. 9 is a diagram showing an example of a configuration of an image sensor IMG5 according to a second embodiment of the present invention.

Hereinafter, a second embodiment of the present invention will be described with reference to the drawings. FIG. 9 is a block diagram showing an example of a configuration of an image sensor IMG5 according to the second embodiment of the present invention. In FIG. 6, the same reference numerals are given or the reference signs including characters and the same numbers are given to the same or corresponding configuration shown in FIG. 3. FIG. 5, FIG. 6, FIG. 7, and FIG. 8 and a description is omitted accordingly.
<Configuration of image sensor IMG5>

The image sensor IMG5 (semiconductor device) shown in FIG. 9 includes m×n pixels P (P[1, 1] to P[m, n]), a timing generator TG n comparators CMP (CMP<1> to CMP<n>), a ramp-wave generator RAMP_GEN, n latches LAT (LAT<1> to ILAT<n>), a grey-code counter COUNTER, and n tail current sources ITAIL (ITAIL<1> to ITAIL<n>). In addition to these, the image sensor IMG5 includes resistors R<1> to R<n>, OB memories MEM_OB (MEM_OB<1> to MEM_OB<n>), video memories MEM_SIG (MEM_SIG<1> to MEM_SIG<n>), a subtractor SUB, and a low-voltage differential-signaling (LVDS) driver that outputs data generated by subtraction.
<Operation of Image Sensor IMG5>

Figure 10:
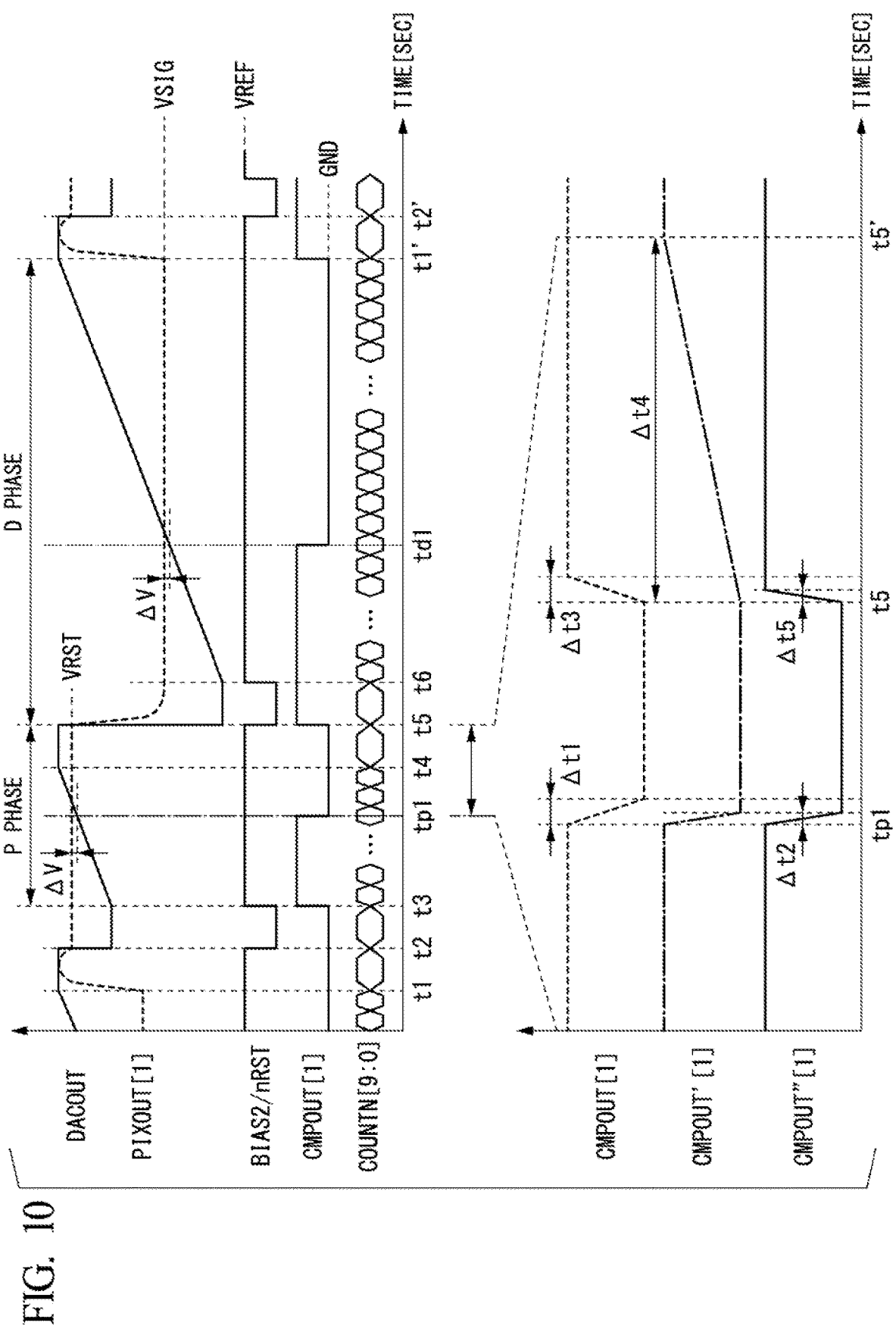
FIG. 10 is a timing chart showing an operation of the image sensor IMG5 according to the second embodiment of the present invention.

Hereinafter, an operation of the image sensor IMG5 shown in FIG. 9 will be described by using FIG. 10. FIG. 10 is a timing chart showing an operation of the image sensor IMG5.

The period of the reading processing for one line is shown on the upper side of FIG. 10 and the period from a time point tp1 to a time point t5 is magnified on the lower side of FIG. 10. The image sensor IMG5 shown in FIG. 9 is basically the same as the image sensor IMG2 shown in FIG. 6, but is different only in terms of the point that a BIAS2/nRST signal is newly added.

In the first embodiment, the level of the DC gate voltage BIAS is a fixed level when the load MOS transistor (active load) $M_{RST}'$ causes the current that is half the current of the tail current source ITAIL to flow in the drain of the pair transistor $M_{SF}'$.

On the other hand, the BIAS2/nRST signal is configured to periodically repeat the BIAS2 level and the "L" level.

Here, the BIAS2 level is the gate voltage VREF causing the drain current of the load MOS transistor $M_{RST}'$ to be less than half of Itail when a sufficient source-drain voltage is applied to the load MOS transistor $M_{RST}'$. The "L" level is the gate voltage causing the drain current of the load MOS transistor $M_{RST}'$ to be greater than half of Itail. In the embodiment, not only the bias circuit is simplified by setting the "L" level to the GND level, but also high-speed response is realized by causing the load MOS transistor $M_{RST}'$ to operate as a switch.

In other words, the gate voltage applied to the load MOS transistor $M_{RST}'$ meets the condition indicated as "nRST<BIAS<BIAS2." Here, nRST is the voltage (for example, GND (0 V)) in the second embodiment, BIAS is the voltage in the first embodiment, and BIAS2 (for example, VREF) is the voltage in the second embodiment. The drain current of the load MOS transistor $M_{RST}'$ meets the condition indicated as "InRST>IBIAS>IBIAS2." Here, the current InRST is the drain current when the gate voltage is nRST, the current IBIAS is the drain current when the gate voltage is BIAS, and the current IBIAS2 is the drain current when the gate voltage is BIAS2.
<Operation in AD-Conversion>

The through-rate $SR_{DN}$ (change rate) in a period in which the falling edge of the output of the comparator is shifted in the timing chart in FIG. 10 is given by the following expression.

$$SR_{DN}=dV/dt=(\text{Ibias}-\text{Itail})/Cp$$

Here, Cp indicates the parasitic capacitance at the input terminal of the inverter.

In design of the first embodiment, the condition indicated as "Ibias=0.5×Itail" is met. Therefore, the through-rate $SR_{DN}1$ (the through-rate $SR_{DN}$ of the waveform CMPOUT [1] in FIG. 10) at a timing at which the output of the comparator is inverted is given by the following expression.

$$SR_{DN}1=(0.5\times\text{Itail}-\text{Itail})/Cp=-(0.5\times\text{Itail})/Cp$$

On the other hand, in design of the comparator according to the embodiment, for example, the condition indicated as "Ibias2=0.01×Itail" is met. Therefore, the through-rate $SR_{DN}2$ (the through-rate $SR_{DN}$ of the waveform CMPOUT' [1] and the waveform CMPOUT"[1] in FIG. 10) at a timing at which the output of the comparator is inverted is given by the following expression.

$$SR_{DN}2=(\text{Ibias2}-\text{Itail})/Cp=(0.01\times\text{Ibias}-\text{Ibias})Cp=-(0.99\times\text{Itail})/Cp$$

In other words, the comparator according to the second embodiment completes determination of voltage in a shorter period of time than the comparator according to the first embodiment. Since the conversion accuracy of the column ADC depends on the accuracy of the time point at which the output of the comparator is inverted, an AD converter having higher conversion accuracy can be realized by using the comparator according to the second embodiment.
[Operation at Time of Reset]

As described above, the determination accuracy of the comparator is improved by setting the value of Ibias to a sufficiently smaller value than Itail. However, the through-rate $SR_{UP}$ (change rate) in a period (reset period of the comparator) in which the rising edge of the output of the comparator is shifted in the timing chart in FIG. 10 is given by the following expression.

$$SR_{UP}=dV/dt=\text{Ibias}/Cp$$

In other words, there is a problem that it takes more time to reset the comparator as the value of Ibias reduces.

The above-described problem is resolved by casing the comparator CMP to operate in a first period (determination period) in which the bias current of the load MOS transistor $M_{RST}'$ (active load) is less than half of the tail current and in a second period (reset period) in which the bias current of the load MOS transistor $M_{RST}'$ is greater than half of the tail current.

Therefore, in the embodiment, the load MOS transistor $M_{RST}'$ of the comparator according to the embodiment may be biased to BIAS2 in the AD-conversion period and may be biased to the GND level in the reset period during which the load MOS transistor $M_{RST}'$ operates as an analog switch in order to cause the bias current of the active load in the second period to be greater than half of the tail current.

The timing chart showing this effect is shown in FIG. 10.

The CMPOUT[1] on the lower side of FIG. 10 is a timing chart showing the response of the comparator in the first embodiment. The CMPOUT'[1] on the lower side of FIG. 10 is a timing chart showing the response output by the comparator in a case in which the bias current of the load MOS transistor $M_{RST}'$ is less than half of the tail current in both the determination period and the reset period. The CMPOUT" [1] on the lower side of FIG. 10 is a timing chart showing the response output by the comparator in a case in which the bias current of the load MOS transistor $M_{RST}'$ is less than half of the tail current in the determination period and is greater than half of the tail current in the reset period.

The change rate $SR_{UP}1$ of voltage in the reset period of CMPOUT[1] is given by the following expression.

$$SR_{UP}1=0.5\times\text{Ibias}/Cp$$

In other words, when design of CMPOUT[1] is used, since Ibias in the reset period is expressed as "Ibias=0.5×Itail," the bias current of the load MOS transistor $M_{RST}'$ in the reset period (second period) of CMPOUT[1] functions at 0.5×Ibias.

The change rate $SR_{UP}2$ of voltage in the reset period of CMPOUT'[1] is given by the following expression.

$$SR_{UP}2=0.01\times\text{Ibias}/Cp$$

In other words, when design of CMPOUT'[1] is used, since Ibias in the reset period is expressed as "Ibias=0.01×Itail," the bias current of the load MOS transistor $M_{RST}'$ in the reset period (second period) of CMPOUT[1] functions at 0.01×Ibias.

The change rate $SR_{UP}3$ of voltage in the reset period of CMPOUT"[1] is given by the following expression.

$$SR_{UP}3=100\times\text{Ibias}/Cp$$

In other words, when design of CMPOUT"[1] is used, since Ibias in the reset period is expressed as, for example. "Ibias=100×Itail." the bias current of the load MOS transistor $M_{RST}'$ in the reset period (second period) of CMPOUT[1] functions at 100×Ibias.

As described above, in the waveform of CMPOUT'[1], a period of time in which the level changes from "H" to "L" is shortened (Δt1 is shortened to be Δt2 as shown in FIG. 10) compared to the waveform of CMPOUT[1]. As described above, in the waveform of CMPOUT"[1], a period of time in which the level changes from "L" to "H" is shortened (Δt3 is shortened to be Δt5 as shown in FIG. 10) compared to the waveform of CMPOUT[1].

In other words, in a case in which the gate voltage of the load MOS transistor $M_{RST}'$ is BIAS2 (BIAS2=nRST>BIAS (the gate voltage in the first embodiment)) in the image sensor IMG5 shown in FIG. 9, the bias current of the load MOS transistor $M_{RST}'$ provided in the signal-processing circuit is less than half of the tail current.

According to this, the speed at which the output of the comparator is inverted is faster compared to a typical comparator and therefore it is possible to store a time point at which the output of the comparator is inverted with higher accuracy than a conventional comparator. Since the accuracy of storing a time point at which the output of the comparator is inverted matches the conversion accuracy of an AD converter, an AD converter with higher accuracy can be provided according to the above-described configuration.

In addition, in a case in which the gate voltage of the load MOS transistor $M_{RST}'$ is BIAS2 (BIAS2>BIAS>nRST) in the image sensor IMG5 shown in FIG. 9, the signal-processing circuit performs a determination operation in the first period in which the bias current of the load MOS transistor $M_{RST}'$ provided in the signal-processing circuit is less than half of the tail current and the signal-processing circuit performs a reset operation in the second period in which the bias current of the load MOS transistor $M_{RST}'$ is greater than half of the tail current. The signal-processing circuit compares the first analog signal output from the element array with comparison voltage generated by the comparison-voltage generation circuit.

According to this, the comparator can be reset at high speed in the second period in which a large bias current flows and therefore it is possible to accelerate the reset speed of an AD converter having a shortcoming that it takes long to reset a comparator. In other words, an AD converter operating with high accuracy and at high speed can be provided.

Third Embodiment

Next, a third embodiment of the present invention will be described with reference to the drawings. FIG. 1I is a schematic diagram outlining the entire configuration of an endoscope system to which the image sensor IMG2 shown in FIG. 6 and the image sensor IMG5 shown in FIG. 9 are applied.

<Configuration of Endoscope System>

Figure 11:
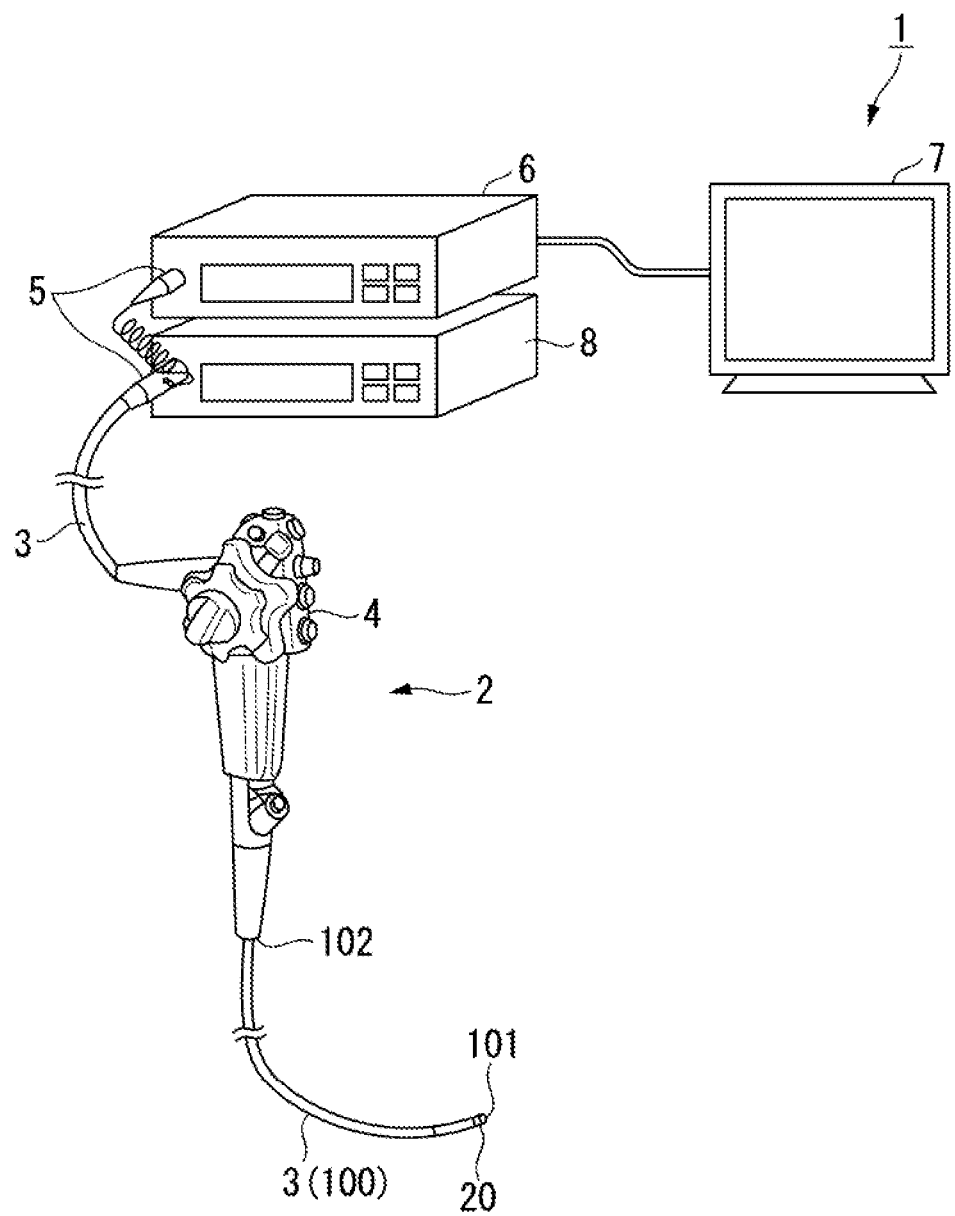
FIG. 11 is a schematic diagram outlining the entire configuration of an endoscope system to which the image sensor IMG2 shown in FIG. 6 and the image sensor IMG5 shown in FIG. 9 are applied.

The endoscope system 1 shown in FIG. 11 includes an endoscope 2 functioning as a source device, a transmission cable 3 functioning as a transmission path, a connector unit 5 functioning as a sink device, a processor 6 (control device), a display device 7, and a light source device 8.

The insertion unit 100 that is a part of the transmission cable 3 is inserted into the body of a subject and the endoscope 2 outputs image data generated by imaging the inside of the body of the subject to the processor 6. The endoscope 2 includes an imaging unit 20 (the image sensor IMG2 shown in FIG. 6 and the image sensor IMG5 shown in FIG. 9) and an operation unit 4. The imaging unit 20 is disposed in the distal end part 101 of the insertion unit 100 that is at one end of the transmission cable 3 and the imaging unit 20 generates the image data that are downlink data. The operation unit 4 is connected to the base end part 102 of the insertion unit 100 and accepts various kinds of operations for the endoscope 2. The image data generated by the imaging unit 20 is output to the connector unit 5 connected by the transmission cable 3 having the length of at least 10 cm.

The connector unit 5 is detachably connected to the processor 6 and the light source device 8, performs predetermined signal processing on the image data output by the imaging unit 20, and outputs the image data to the processor 6.

The processor 6 performs predetermined image processing on the imaging signal input from the connector unit 5 and controls the entire endoscope system 1.

The display device 7 displays an image corresponding to the image signal on which image processing has been performed by the processor 6. In addition, the display device 7 displays various pieces of information related to the endoscope system 1.

The light source device 8 is constituted by, for example, a halogen lamp, a light-emitting diode (LED), or the like and emits illumination light from the distal end part 101 of the insertion unit 100 of the endoscope 2 to the subject via the transmission cable 3 under the control by the processor 6.

<Configuration of Endoscope>

First, the endoscope 2 will be described.

As shown in FIG. 1, the endoscope 2 includes the imaging unit 20, the transmission cable 3, and the connector unit 5.

The imaging unit 20 includes the OB memory MEM_OB that holds the AD-conversion result of OB output, the video memory MEM_SIG that holds the AD-conversion result of video output, the subtractor SUB that performs subtraction using these two values of the AD-conversion results, and the low-voltage differential-signaling (LVDS) driver as described by using the image sensor IMG2 shown in FIG. 6.

The OB memories MEM_OB<1> to MEM_OB<n> hold counting data COUNTN[9: 0] (counting data held by each of the latches LAT<1> to LAT<n>) at a timing (time point tp1 shown in FIG. 4) at which the comparators CMP (CMP<1> to CMP<n>) cause the determination signals CMP_OUT[1] to CMP_OUT[n] to be inverted regarding the P phase (analog voltage=VRST).

In addition, the video memories MEM_SIG<1> to MEM_SIG<n> hold the counting data COUNTN[9: 0] (counting data held by each of the latches LAT<1> to LAT<n>) at a timing (time point td1 shown in FIG. 4) at which the comparators CMP (CMP<1> to CMP<n>) cause the determination signals CMP_OUT[1] to CMP_OUT[n] to be inverted regarding the D phase (analog voltage=VSIG).

In addition, the subtractor SUB subtracts the counting data COUNTN[9: 0] stored on the OB memories MEM_OB<1> to MEM_OB<n> from the counting data COUNTN[9: 0] stored on the respective video memories MEM_SIG<1> to MEM_SIG<n>, thus generating image data.

Furthermore, low-voltage differential signals (LVDS), which are interfaces used for transmitting signals having a small amplitude at high speed, are applied to the LVDS driver and an input signal (image data) is input to the LVDS driver. The LVDS driver converts the input signal into a differential signal that has a signal level ranging front the positive (+) direction to the negative (−) direction and also has decreased amplitude, for example, less than or equal to 100 mV and outputs the differential signal to an external device through a pair of output-signal lines (two transmission lines).

The transmission cable 3 is constituted by using, for example, a coaxial cable or the like and includes a transmission line (power source line) transmitting a power source voltage, a ground line, and a pair of transmission lines transmitting the differential signal. The transmission cable 3, for example, has the length of 10 cm or more and connects the imaging unit 20 and the connector unit 5 together.

As described above, by applying the imaging unit 20 (the image sensor IMG2 shown in FIG. 6 and the image sensor IMG5 shown in FIG. 9) to an endoscope system, the AD-conversion result of OB output and the AD-conversion result of video output can be transmitted as the differential signal by performing transmission once although the AD-conversion results are transmitted independently of each other by performing transmission twice in the image sensor described in the first embodiment. In other words, the transfer speed of data that the LVDS driver should output can be reduced, and therefore, transmission of video signals by using a thin transmission cable can be realized.

That is, the imaging unit 20 (the image sensor IMG2 shown in FIG. 6 and the image sensor IMG5 shown in FIG. 9) is an image sensor (semiconductor device) that is applied to the endoscope 2 including the insertion unit 100 and the connector unit 5 and is provided in the distal end part of the insertion unit 100. The insertion unit 100 is capable of being inserted into a subject and the connector unit 5 is detachably connected to the processor 6 (control device) that executes predetermined image processing.

In addition, the imaging unit 20 further includes the OB memory MEM_OB (first memory), the video memory MEM_SIG (second memory), the subtractor SUB, and the LVDS driver.

Here, the OB memory MEM_OB (first memory) stores digital data corresponding to the input analog voltage at a timing at which the value of the second analog signal and the comparison voltage $V_{SF}'$ match each other when the analog voltage is at the reset voltage VRST. The video memory MEM_SIG (second memory) stores digital data corresponding to the input analog voltage at a timing at which the value of the second analog signal and the comparison voltage $V_{SF}'$ match each other when the analog voltage is at the video voltage VSIG The subtractor SUB subtracts digital data corresponding to the pixel P (element) among the digital data stored on the OB memory MEM_OB from the digital data corresponding to the same pixel P (element) stored on the video memory MEM_SIG, thus generating image data. The LVDS driver converts the image data generated by the subtractor SUB into the differential signal and transmits the converted differential signal to the connector unit 5 through two transmission lines.

In this way, the imaging unit 20 (the image sensor IMG2 shown in FIG. 6 and the image sensor IMG5 shown in FIG. 9) can be miniaturized by realizing a comparator that can be used in a smaller column circuit than a conventional one without providing a capacitor and a special power source, and also allows a thinner cable by reducing the transfer rate of video signals. Therefore, an image sensor suitable for use in an endoscope system can be provided.

While preferred embodiments of the invention have been described and shown above, it should be understood that these are examples of the invention and are not to be considered as limiting. Additions, omissions, substitutions, and other modifications can be made without departing from the spirit or scope of the present invention.

Accordingly, the invention is not to be considered as being limited by the foregoing description, and is only limited by the scope of the appended claims.

What is claimed is:

1. A semiconductor device, comprising:
  a plurality of element arrays, wherein each element array included in the plurality of element arrays is selectively connected to a vertical signal line and includes an amplification transistor configured to output a first analog signal on the basis of an input analog voltage and an actual value of variation of a characteristic value of each element array included in the plurality of element arrays;
  a signal-processing circuit connected to the vertical signal line; and
  a comparison-voltage generation circuit configured to output a gradually increasing or gradually decreasing comparison voltage to the signal-processing circuit,
  wherein the signal-processing circuit includes a storage circuit and is configured to compare the first analog signal with the comparison voltage and store a timing at which the comparison voltage and a value of a second analog signal generated by adding a predetermined absolute value to the first analog signal match each other onto the storage circuit,
  the signal-processing circuit includes a differential transistor forming a differential pair with the amplification transistor of the element array included in the plurality of element arrays when the element array and the signal-processing circuit are connected to each other by the vertical signal line,
  the signal-processing circuit is configured to output a difference between the comparison voltage input to the differential transistor and the analog voltage input to the amplification transistor, and a level-shift circuit that is provided between the amplification transistor and a tail current source of the signal-processing circuit and is configured to cause a source voltage of the amplification transistor to be higher than a source voltage of the differential transistor.

2. The semiconductor device according to claim 1, wherein a threshold voltage of the differential transistor is smaller than a threshold voltage of the amplification transistor.

3. The semiconductor device according to claim 1, wherein an aspect ratio of W (channel width)/L (channel length) of the differential transistor is greater than an aspect ratio of W/L of the amplification transistor.

4. The semiconductor device according to claim 1, wherein a back gate terminal of the differential transistor is biased to the same voltage as that of a source terminal of the differential transistor, and
a back gate terminal of the amplification transistor is biased to a lower voltage than a voltage of a source terminal of the differential transistor.

5. The semiconductor device according to claim 1, wherein a bias current of an active load provided in the signal-processing circuit is smaller than half of a tail current output by a tail current source of the signal-processing circuit.

6. The semiconductor device according to claim 5, wherein the signal-processing circuit is configured to compare the first analog signal with the comparison voltage in a first period in which the bias current of the active load is less than half of the tail current, and
the signal-processing circuit is configured to perform a reset operation in a second period in which the bias current of the active load is greater than half of the tail current.

7. The semiconductor device according to claim 1, wherein the predetermined absolute value is greater than or equal to 30 mV and less than or equal to 500 mV.

8. The semiconductor device according to claim 1, wherein the semiconductor device is applied to an endoscope including an insertion unit capable of being inserted into a subject and a connector unit detachably connected to a control device that executes predetermined image processing and is provided in a distal end part of the insertion unit, and
the semiconductor device further comprises:
a first memory configured to store digital data corresponding to the analog voltage at a timing at which the value of the second analog signal and the comparison voltage match each other when the analog voltage is at reset voltage;
a second memory configured to store digital data corresponding to the analog voltage at a timing at which the value of the second analog signal and the comparison voltage match each other when the analog voltage is at video voltage;
a subtractor configured to subtract digital data corresponding to an element in the plurality of element arrays among digital data stored on the first memory from the digital data corresponding to the element stored on the second memory so as to generate image data; and
a low-voltage differential-signaling (LVDS) driver configured to convert the image data into a differential signal and transmit the differential signal to the connector unit through two transmission lines.

9. A semiconductor device, comprising:
a plurality of element arrays, wherein each element array included in the plurality of element arrays is selectively connected to a vertical signal line and includes an amplification transistor configured to output a first analog signal on the basis of an input analog voltage and an actual value of variation of a characteristic value of each element array included in the plurality of element arrays;
a signal-processing circuit connected to the vertical signal line; and
a comparison-voltage generation circuit configured to output a gradually increasing or gradually decreasing comparison voltage to the signal-processing circuit,
wherein the signal-processing circuit includes a storage circuit and is configured to compare the first analog signal with the comparison voltage and store a timing at which the comparison voltage and a value of a second analog signal generated by adding a predetermined absolute value to the first analog signal match each other onto the storage circuit,
the signal-processing circuit includes a differential transistor forming a differential pair with the amplification transistor of the element array included in the plurality of element arrays when the element array and the signal-processing circuit are connected to each other by the vertical signal line,
the signal-processing circuit is configured to output a difference between the comparison voltage input to the differential transistor and the analog voltage input to the amplification transistor,
the signal-processing circuit is configured to compare the first analog signal with the comparison voltage in a first period in which the bias current of the active load is less than half of the tail current, and
the signal-processing circuit is configured to perform a reset operation in a second period in which the bias current of the active load is greater than half of the tail current.

10. The semiconductor device according to claim 9, wherein a threshold voltage of the differential transistor is smaller than a threshold voltage of the amplification transistor.

11. The semiconductor device according to claim 9, wherein an aspect ratio of W (channel width)/L (channel length) of the differential transistor is greater than an aspect ratio of W/L of the amplification transistor.

12. The semiconductor device according to claim 9, wherein a back gate terminal of the differential transistor is biased to the same voltage as that of a source terminal of the differential transistor, and
a back gate terminal of the amplification transistor is biased to a lower voltage than a voltage of a source terminal of the differential transistor.

13. The semiconductor device according to claim 9, wherein a bias current of an active load provided in the signal-processing circuit is smaller than half of a tail current output by a tail current source of the signal-processing circuit.

14. The semiconductor device according to claim 9, wherein the predetermined absolute value is greater than or equal to 30 mV and less than or equal to 500 mV.

15. The semiconductor device according to claim 9, wherein the semiconductor device is applied to an endoscope including an insertion unit capable of being inserted into a subject and a connector unit detachably connected to a control device that executes predetermined image processing and is provided in a distal end part of the insertion unit, and the semiconductor device further comprises:
- a first memory configured to store digital data corresponding to the analog voltage at a timing at which the value of the second analog signal and the comparison voltage match each other when the analog voltage is at reset voltage;
- a second memory configured to store digital data corresponding to the analog voltage at a timing at which the value of the second analog signal and the comparison voltage match each other when the analog voltage is at video voltage;
- a subtractor configured to subtract digital data corresponding to an element in the plurality of element arrays among digital data stored on the first memory from the digital data corresponding to the element stored on the second memory so as to generate image data; and
- a low-voltage differential-signaling (LVDS) driver configured to convert the image data into a differential signal and transmit the differential signal to the connector unit through two transmission lines.

* * * * *